US006683052B1

United States Patent
Thiam et al.

(10) Patent No.: US 6,683,052 B1
(45) Date of Patent: Jan. 27, 2004

(54) LIPOPEPTIDES CONTAINING AN INTERFERON-γ FRAGMENT, AND USES THEREOF IN PHARMACEUTICAL COMPOSITIONS

(75) Inventors: Kader Thiam, Lille (FR); Claude Auriault, Nomain (FR); Helene Gras-Masse, Merignies (FR); Estelle Loing, Lille (FR); Claudie Verwaerde, Lille (FR); Jean Gerard Guillet, Vanves (FR)

(73) Assignees: Institut National de la Sante et de la Recherche Medicale Inserm, Paris Cedex (FR); Institut Pasteur de Lille, Lille (FR); Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 09/601,729
(22) PCT Filed: Feb. 5, 1999
(86) PCT No.: PCT/FR99/00259
§ 371 (c)(1),
(2), (4) Date: Nov. 20, 2000
(87) PCT Pub. No.: WO99/40113
PCT Pub. Date: Aug. 12, 1999

(30) Foreign Application Priority Data

Feb. 6, 1998 (FR) ............................. 98 01439

(51) Int. Cl.$^7$ .................. C07K 14/57; A61K 47/48; A61K 38/21
(52) U.S. Cl. .................. 514/12; 514/13; 424/85.5; 424/184.1; 424/450; 435/325; 530/324; 530/326; 530/334; 530/344; 530/351
(58) Field of Search ............... 424/85.5, 184.1, 424/450; 435/325; 514/12, 13; 530/324, 326, 334, 344, 351

(56) References Cited

U.S. PATENT DOCUMENTS 5,270,038 A * 12/1993 Klimpel et al.

FOREIGN PATENT DOCUMENTS

| EP | 0 236 987 | * | 9/1987 |
| EP | 0 510 356 | * | 10/1992 |
| EP | 0 593 868 | * | 4/1994 |
| WO | WO 97/18832 | * | 5/1997 |

OTHER PUBLICATIONS

By K. Thiam et al., Unrestricted Agonist Activity on Murine and Human Cells of a Lipopeptide Derived from IFN–γ, Biochemical and Biophysical Research Communications, vol. 253, No. 3, Dec. 1998, pp. 639–647.*
By F. Rouaix et al., "Effect of a lipopeptidic formulation on macrophage activation and peptide presentation to T cells", VACCINE, vol. 12/13, 1994, pp. 1209–1214.*
By B. Deprez et al., "Comparative efficiency of simple lipopetide constructs for in vivo induction of virus–specific CTL", VACCINE, vol. 14, No. 5, 1996, pp. 375–382.*

* cited by examiner

Primary Examiner—Christopher S. F. Low
Assistant Examiner—Chih-Min Kam
(74) Attorney, Agent, or Firm—Young & Thompson

(57) ABSTRACT

The invention concerns any lipopeptide characterized in that it comprises: a peptide part comprising the peptide sequence consisting of about 30 to about 50 of the last contiguous amino acids of the interferon-γ (IFN-γ) C-terminal end of mammals, whereof, if required, the last 3 to 20 amino acids have been suppressed; and one or several lipophilic parts comprising C4–C20 chain of carbon atoms, saturated or unsaturated, linear or branched, or a steroid group. The invention also concerns any lipopeptide such as defined above containing one or several CD8, and/or CD4, and/or B epitopes. The invention further concerns medicines or vaccines containing any polypeptide such as defined above.

Figure 1:
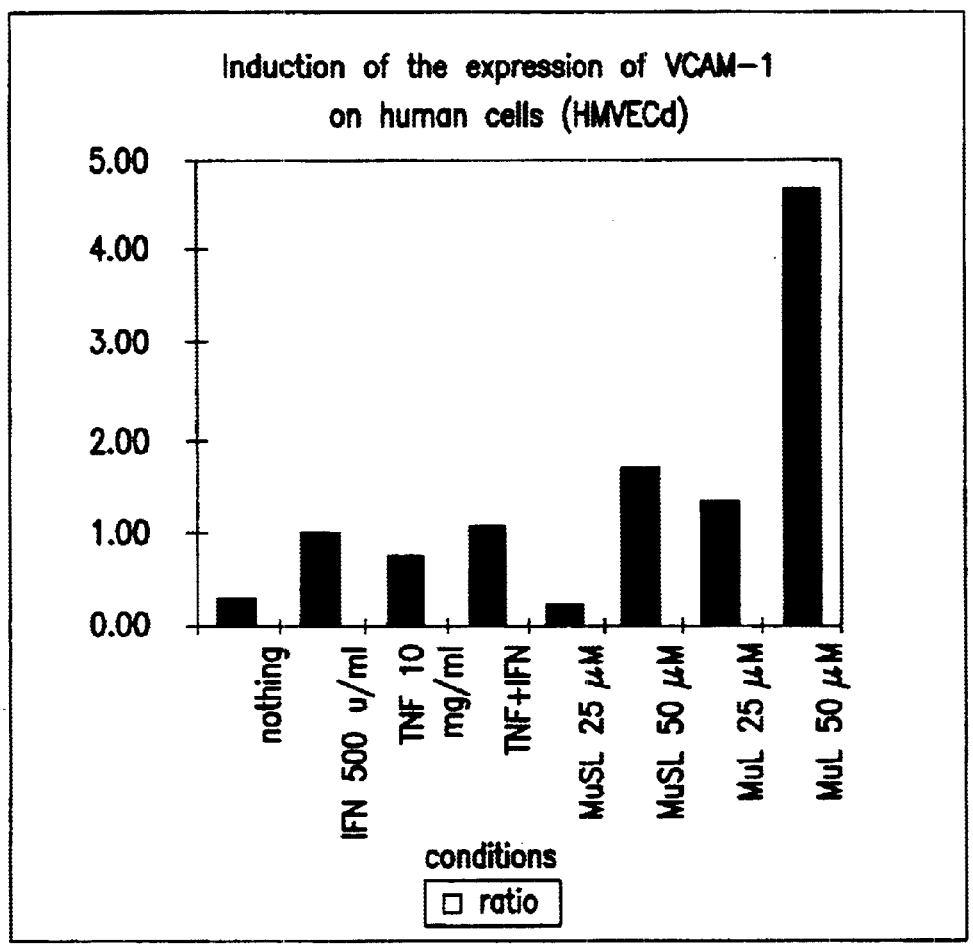

11 Claims, 11 Drawing Sheets ial activity observed in the

SEQUENCE LISTING

<160> NUMBER OF SEQ ID NOS: 281

<210> SEQ ID NO 1
<211> LENGTH: 20
<212> TYPE: PRT
<213> ORGANISM: Mus sp.

<400> SEQUENCE: 1

```
Ile Arg Val Val His Gln Leu Leu Pro Glu Ser Ser Leu Arg Lys Arg
  1               5                  10                  15

Lys Arg Ser Arg
            20
```

<210> SEQ ID NO 2
<211> LENGTH: 143
<212> TYPE: PRT
<213> ORGANISM: Homo sapiens

<400> SEQUENCE: 2

```
Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
             35                  40                  45

Ile Val Ser Phe Tyr Phe Lys Leu Phe Lys Asn Phe Lys Asp Asp Gln
         50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala Ser Gln
        130                 135                 140
```

<210> SEQ ID NO 3
<211> LENGTH: 143
<212> TYPE: PRT
<213> ORGANISM: Bovine sp.

<400> SEQUENCE: 3

```
Gln Gly Gln Phe Phe Arg Glu Ile Glu Asn Leu Lys Glu Tyr Phe Asn
  1               5                  10                  15

Ala Ser Ser Pro Asp Val Ala Lys Gly Gly Pro Leu Phe Ser Glu Ile
             20                  25                  30

Leu Lys Asn Trp Lys Asp Glu Ser Asp Lys Lys Ile Ile Gln Ser Gln
             35                  40                  45

Ile Val Ser Phe Tyr Phe Lys Leu Phe Glu Asn Leu Lys Asp Asn Gln
         50                  55                  60

Val Ile Gln Arg Ser Met Asp Ile Ile Lys Gln Asp Met Phe Gln Lys
 65                  70                  75                  80

Phe Leu Asn Gly Ser Ser Glu Lys Leu Glu Asp Phe Lys Lys Leu Ile
                 85                  90                  95

Gln Ile Pro Val Asp Asp Leu Gln Ile Gln Arg Lys Ala Ile Asn Glu
                100                 105                 110

Leu Ile Lys Val Met Asn Asp Leu Ser Pro Lys Ser Asn Leu Arg Lys
            115                 120                 125

Arg Lys Arg Ser Gln Asn Leu Phe Arg Gly Arg Arg Ala Ser Met
        130                 135                 140
```

<210> SEQ ID NO 4

```
<211> LENGTH: 143
<212> TYPE: PRT
<213> ORGANISM: Callithrix jacchus

<400> SEQUENCE: 4

Gln Asp Pro Tyr Val Lys Glu Ala Glu Asn Leu Lys Lys Tyr Phe Asn
 1               5                  10                  15

Ala Gly Asp Ser Asp Val Ala Asp Asn Gly Thr Leu Phe Leu Asp Ile
             20                  25                  30

Leu Arg Thr Trp Arg Glu Gly Asp Arg Lys Ile Met Gln Ser Gln
         35                  40                  45

Ile Ile Ser Phe Tyr Phe Lys Leu Phe Lys Asn Phe Lys Asp Asn Gln
     50                  55                  60

Ser Ile Gln Lys Ser Met Glu Thr Ile Lys Glu Asp Met Asn Val Lys
 65                  70                  75                  80

Phe Phe Asn Ser Asn Lys Arg Lys Gln Asp Asp Phe Glu Arg Leu Thr
                 85                  90                  95

Asn Tyr Ser Val Asn Asp Leu Asn Val Gln Arg Lys Ala Ile His Glu
            100                 105                 110

Leu Ile Gln Val Met Ala Glu Leu Ser Pro Ala Pro Lys Ile Gly Lys
        115                 120                 125

Arg Arg Arg Ser Gln Thr Leu Phe Arg Gly Arg Ala Ser Gln
    130                 135                 140

<210> SEQ ID NO 5
<211> LENGTH: 142
<212> TYPE: PRT
<213> ORGANISM: Cercocebus torquatius

<400> SEQUENCE: 5

Gln Asp Pro Tyr Val Lys Glu Ala Glu Asn Leu Lys Lys Tyr Phe Asn
 1               5                  10                  15

Ala Gly Asp Pro Asp Val Ala Asp Asn Gly Thr Leu Phe Leu Asp Ile
             20                  25                  30

Leu Arg Asn Trp Lys Glu Glu Ser Asp Arg Lys Ile Met Gln Ser Gln
         35                  40                  45

Ile Val Ser Phe Tyr Phe Lys Leu Phe Lys Ser Phe Lys Asp Asp Gln
     50                  55                  60

Arg Ile Gln Lys Ser Val Glu Thr Ile Lys Glu Asp Ile Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Val His Glu
            100                 105                 110

Leu Ile Gln Val Met Ala Glu Leu Ser Pro Ala Ala Lys Ile Gly Lys
        115                 120                 125

Arg Lys Arg Ser Gln Thr Phe Arg Gly Arg Arg Ala Ser Gln
    130                 135                 140

<210> SEQ ID NO 6
<211> LENGTH: 145
<212> TYPE: PRT
<213> ORGANISM: Canis familiaris

<400> SEQUENCE: 6

Tyr Cys Gln Ala Met Phe Phe Lys Glu Ile Glu Asn Leu Lys Glu Tyr
 1               5                  10                  15
```

```
Phe Asn Ala Ser Asn Pro Asp Val Ser Asp Gly Gly Ser Leu Phe Val
                20                  25                  30

Asp Ile Leu Lys Lys Trp Arg Glu Glu Ser Asp Lys Thr Ile Ile Gln
            35                  40                  45

Ser Gln Ile Val Ser Phe Tyr Leu Lys Leu Phe Asp Asn Phe Lys Asp
        50                  55                  60

Asn Gln Ile Ile Gln Arg Ser Met Asp Thr Ile Lys Glu Asp Met Leu
65                  70                  75                  80

Gly Lys Phe Leu Asn Ser Ser Thr Ser Lys Arg Glu Asp Phe Leu Lys
                85                  90                  95

Leu Ile Gln Ile Pro Val Asn Asp Leu Gln Val Gln Arg Lys Ala Ile
            100                 105                 110

Asn Glu Leu Ile Lys Val Met Asn Asp Leu Ser Pro Arg Ser Asn Leu
        115                 120                 125

Arg Lys Arg Lys Arg Ser Gln Asn Leu Phe Arg Gly Arg Arg Ala Ser
130                 135                 140

Lys
145

<210> SEQ ID NO 7
<211> LENGTH: 144
<212> TYPE: PRT
<213> ORGANISM: Felis sp.

<400> SEQUENCE: 7

Gln Ala Met Phe Phe Lys Glu Ile Glu Glu Leu Lys Gly Tyr Phe Asn
1               5                   10                  15

Ala Ser Asn Pro Asp Val Ala Asp Gly Gly Ser Leu Phe Val Asp Ile
                20                  25                  30

Leu Lys Asn Trp Lys Glu Glu Ser Asp Lys Thr Ile Ile Gln Ser Gln
            35                  40                  45

Ile Val Ser Phe Tyr Leu Lys Met Phe Glu Asn Leu Lys Asp Asp Asp
        50                  55                  60

Gln Arg Ile Gln Arg Ser Met Asp Thr Ile Lys Glu Asp Met Leu Asp
65                  70                  75                  80

Lys Leu Leu Asn Thr Ser Ser Lys Arg Asp Asp Phe Leu Lys Leu
                85                  90                  95

Ile Gln Ile Pro Val Asn Asp Leu Gln Val Gln Arg Lys Ala Ile Asn
            100                 105                 110

Glu Leu Phe Lys Val Met Asn Asp Leu Ser Pro Arg Ser Asn Leu Arg
        115                 120                 125

Lys Arg Lys Arg Ser Gln Asn Leu Phe Arg Gly Arg Arg Ala Ser Lys
130                 135                 140

<210> SEQ ID NO 8
<211> LENGTH: 143
<212> TYPE: PRT
<213> ORGANISM: Cervidae sp.

<400> SEQUENCE: 8

Gln Gly Pro Phe Phe Lys Glu Ile Glu Asn Leu Lys Glu Tyr Phe Asn
1               5                   10                  15

Ala Ser Asn Pro Asp Val Ala Glu Gly Gly Pro Leu Phe Ile Glu Ile
                20                  25                  30

Leu Lys Asn Trp Lys Glu Glu Ser Asp Arg Lys Ile Ile Gln Ser Gln
            35                  40                  45
```

```
Ile Val Ser Phe Tyr Phe Lys Leu Phe Glu Asn Phe Lys Asp Asn Gln
            50                  55                  60

Val Ile Gln Arg Ser Val Asp Ile Ile Lys Gln Asp Met Phe Gln Lys
 65                  70                  75                  80

Phe Leu Asn Gly Ser Ser Glu Lys Leu Glu Asp Phe Lys Lys Leu Ile
                    85                  90                  95

Gln Ile Ser Val Asp Asp Met Gln Ile Gln Arg Lys Ala Ile Asn Glu
                100                 105                 110

Leu Ile Lys Val Met Asn Asp Leu Ser Pro Lys Ser Asn Leu Ile Lys
                115                 120                 125

Arg Lys Arg Ser Gln Asn Leu Phe Arg Gly Arg Ala Ser Met
130                 135                 140
```

<210> SEQ ID NO 9
<211> LENGTH: 140
<212> TYPE: PRT
<213> ORGANISM: Gallus sp.

<400> SEQUENCE: 9

```
Leu Asn Leu Val Gln Leu Gln Asp Asp Ile Asp Lys Leu Lys Ala Asp
  1               5                  10                  15

Phe Asn Ser Ser His Ser Asp Val Ala Asp Gly Gly Pro Ile Ile Val
                 20                  25                  30

Glu Lys Leu Lys Asn Trp Thr Glu Arg Asn Glu Lys Arg Ile Ile Leu
             35                  40                  45

Ser Gln Ile Val Ser Met Tyr Leu Glu Met Leu Glu Asn Thr Asp Lys
 50                  55                  60

Ser Lys Pro His Ile Lys His Ile Ser Glu Glu Leu Tyr Thr Leu Lys
 65                  70                  75                  80

Asn Asn Leu Pro Asp Gly Val Lys Lys Val Lys Asp Ile Met Asp Leu
                    85                  90                  95

Ala Lys Leu Pro Met Asn Asp Leu Arg Ile Gln Arg Lys Ala Ala Asn
                100                 105                 110

Glu Leu Phe Ser Ile Leu Gln Lys Leu Val Asp Pro Pro Ser Phe Lys
                115                 120                 125

Arg Lys Arg Ser Gln Ser Gln Arg Arg Cys Asn Cys
130                 135                 140
```

<210> SEQ ID NO 10
<211> LENGTH: 143
<212> TYPE: PRT
<213> ORGANISM: Equus caballus

<400> SEQUENCE: 10

```
Gln Ala Ala Phe Phe Lys Glu Ile Glu Asn Leu Lys Glu Tyr Phe Asn
  1               5                  10                  15

Ala Ser Asn Pro Asp Val Gly Asp Gly Gly Pro Leu Phe Leu Asp Ile
                 20                  25                  30

Leu Lys Asn Trp Lys Glu Asp Ser Asp Lys Lys Ile Ile Gln Ser Gln
             35                  40                  45

Ile Val Ser Phe Tyr Phe Lys Leu Phe Glu Asn Leu Lys Asp Asn Gln
 50                  55                  60

Val Ile Gln Lys Ser Met Asp Thr Ile Lys Glu Asp Leu Phe Val Lys
 65                  70                  75                  80

Phe Phe Asn Ser Ser Thr Ser Lys Leu Glu Asp Phe Gln Lys Leu Ile
                    85                  90                  95
```

```
Gln Ile Pro Val Asn Asp Leu Lys Val Gln Arg Lys Ala Ile Ser Glu
            100                 105                 110

Leu Ile Lys Val Met Asn Asp Leu Ser Pro Lys Ala Asn Leu Arg Lys
            115                 120                 125

Arg Lys Arg Ser Gln Asn Pro Phe Arg Gly Arg Arg Ala Leu Gln
            130                 135                 140
```

<210> SEQ ID NO 11
<211> LENGTH: 142
<212> TYPE: PRT
<213> ORGANISM: Macaca sp.

<400> SEQUENCE: 11

```
Gln Asp Pro Tyr Val Lys Glu Ala Glu Asn Leu Lys Lys Tyr Phe Asn
  1               5                  10                  15

Ala Gly Asp Pro Asp Val Ala Asp Asn Gly Thr Leu Phe Leu Asp Ile
             20                  25                  30

Leu Arg Asn Trp Lys Glu Glu Ser Asp Arg Lys Ile Met Gln Ser Gln
             35                  40                  45

Ile Val Ser Phe Tyr Phe Lys Leu Phe Lys Asn Phe Lys Asp Asp Gln
 50                  55                  60

Arg Ile Gln Lys Ser Val Glu Thr Ile Lys Glu Asp Ile Asn Val Lys
 65                  70                  75                  80

Phe Phe Asn Ser Asn Lys Lys Arg Asp Asp Phe Glu Lys Leu Thr
             85                  90                  95

Asn Tyr Ser Val Thr Asp Ser Asn Val Gln Arg Lys Ala Val His Glu
             100                 105                 110

Leu Ile Gln Val Met Ala Glu Leu Ser Pro Ala Ala Lys Ile Gly Lys
             115                 120                 125

Arg Lys Arg Ser Gln Met Phe Arg Gly Arg Arg Ala Ser Gln
             130                 135                 140
```

<210> SEQ ID NO 12
<211> LENGTH: 143
<212> TYPE: PRT
<213> ORGANISM: Sus scrofa

<400> SEQUENCE: 12

```
Gln Ala Pro Phe Phe Lys Glu Ile Thr Ile Leu Lys Asp Tyr Phe Asn
  1               5                  10                  15

Ala Ser Thr Ser Asp Val Pro Asn Gly Gly Pro Leu Phe Leu Glu Ile
             20                  25                  30

Leu Lys Asn Trp Lys Glu Glu Ser Asp Lys Lys Ile Ile Gln Ser Gln
             35                  40                  45

Ile Val Ser Phe Tyr Phe Lys Phe Phe Glu Ile Phe Lys Asp Asn Gln
 50                  55                  60

Ala Ile Gln Arg Ser Met Asp Val Ile Lys Gln Asp Met Phe Gln Arg
 65                  70                  75                  80

Phe Leu Asn Gly Ser Ser Gly Lys Leu Asn Asp Phe Glu Lys Leu Ile
             85                  90                  95

Lys Ile Pro Val Asp Asn Leu Gln Ile Gln Arg Lys Ala Ile Ser Glu
             100                 105                 110

Leu Ile Lys Val Met Asn Asp Leu Ser Pro Arg Ser Asn Leu Arg Lys
             115                 120                 125

Arg Lys Arg Ser Gln Thr Met Phe Gln Gly Gln Arg Ala Ser Lys
             130                 135                 140
```

<210> SEQ ID NO 13
<211> LENGTH: 144
<212> TYPE: PRT
<213> ORGANISM: Oryctolagus cuniculus

<400> SEQUENCE: 13

Gln Asp Thr Leu Thr Arg Glu Thr Glu His Leu Lys Ala Tyr Leu Lys
 1               5                  10                  15

Ala Asn Thr Ser Asp Val Ala Asn Gly Gly Pro Leu Phe Leu Asn Ile
            20                  25                  30

Leu Arg Asn Trp Lys Glu Glu Ser Asp Asn Lys Ile Ile Gln Ser Gln
        35                  40                  45

Ile Val Ser Phe Tyr Phe Lys Leu Phe Asp Asn Leu Lys Asp His Glu
    50                  55                  60

Val Ile Lys Lys Ser Met Glu Ser Ile Lys Glu Asp Ile Phe Val Lys
65                  70                  75                  80

Phe Phe Asn Ser Asn Leu Thr Lys Met Asp Asp Phe Gln Asn Leu Thr
                85                  90                  95

Arg Ile Ser Val Asp Asp Arg Leu Val Gln Arg Lys Ala Val Ser Glu
            100                 105                 110

Leu Ser Asn Val Leu Asn Phe Leu Ser Pro Lys Ser Asn Leu Lys Lys
        115                 120                 125

Arg Lys Arg Ser Gln Thr Leu Phe Arg Gly Arg Arg Ala Ser Lys Tyr
    130                 135                 140

<210> SEQ ID NO 14
<211> LENGTH: 143
<212> TYPE: PRT
<213> ORGANISM: Ovis sp.

<400> SEQUENCE: 14

Gln Gly Pro Phe Phe Lys Glu Ile Glu Asn Leu Lys Glu Tyr Phe Asn
 1               5                  10                  15

Ala Ser Asn Pro Asp Val Ala Lys Gly Gly Pro Leu Phe Ser Glu Ile
            20                  25                  30

Leu Lys Asn Trp Lys Glu Glu Ser Asp Lys Lys Ile Ile Gln Ser Gln
        35                  40                  45

Ile Val Ser Phe Tyr Phe Lys Leu Phe Glu Asn Leu Lys Asp Asn Gln
    50                  55                  60

Val Ile Gln Arg Ser Met Asp Ile Ile Lys Gln Asp Met Phe Gln Lys
65                  70                  75                  80

Phe Leu Asn Gly Ser Ser Glu Lys Leu Glu Asp Phe Lys Arg Leu Ile
                85                  90                  95

Gln Ile Pro Val Asp Asp Leu Gln Ile Gln Arg Lys Ala Ile Asn Glu
            100                 105                 110

Leu Ile Lys Val Met Asn Asp Leu Ser Pro Lys Ser Asn Leu Arg Lys
        115                 120                 125

Arg Lys Arg Ser Gln Asn Leu Phe Arg Gly Arg Arg Ala Ser Met
    130                 135                 140

<210> SEQ ID NO 15
<211> LENGTH: 143
<212> TYPE: PRT
<213> ORGANISM: Mus montanus

<400> SEQUENCE: 15

Gln Asp Thr Val Asn Lys Glu Ile Glu Asp Leu Lys Gly Tyr Phe Asn

```
                1               5                      10                      15
          Ala Ser Asn Ser Asn Val Ser Asp Gly Gly Ser Leu Phe Leu Asp Ile
                           20                      25                      30

Leu Asp Lys Trp Lys Glu Glu Ser Asp Lys Lys Val Ile Gln Ser Gln
                           35                      40                      45

Val Val Ser Phe Tyr Phe Lys Leu Phe Glu His Leu Lys Asp Asn Lys
                   50                      55                      60

Asn Ile Gln Arg Ser Met Asp Thr Ile Lys Gly Asp Leu Phe Ala Lys
           65                      70                      75                      80

Phe Phe Asn Ser Ser Thr Asn Lys Leu Gln Asp Phe Leu Lys Val Ser
                               85                      90                      95

Gln Val Gln Val Asn Asp Leu Lys Ile Gln Arg Lys Ala Val Ser Glu
                           100                     105                     110

Leu Lys Lys Val Met Asn Asp Leu Leu Pro His Ser Thr Leu Arg Lys
                       115                     120                     125

Arg Lys Arg Ser Gln Ser Ser Ile Arg Gly Arg Arg Ala Ser Lys
           130                     135                     140

<210> SEQ ID NO 16
<211> LENGTH: 151
<212> TYPE: PRT
<213> ORGANISM: Meriones unguiculatus

<400> SEQUENCE: 16

Gln Val Pro Ile Ile Glu Glu Ile Glu Asn Leu Lys Arg Tyr Phe Asn
           1               5                      10                      15

Ser Ser Asn Ser Ala Val Gly Asp Ser Lys Asp Val Val Leu His Val
                           20                      25                      30

Leu Arg Asn Trp Gln Glu Asp Gly Asp Thr Lys Val Ile Asp Val Gln
                           35                      40                      45

Ile Val Ser Phe Tyr Phe Lys Leu Phe Glu Ala Leu Lys Gly Asn Gln
                   50                      55                      60

Ala Ile Glu Lys Ser Ile Asn Ala Ile Arg Ala Asp Leu Ile Ala Asn
           65                      70                      75                      80

Phe Phe Asn Asn Ser Glu Ala Lys Tyr Asp Gly Phe Met Ser Ile Met
                               85                      90                      95

Lys Ile Glu Val Asn Asp Pro Gln Ile Gln Ser Lys Ala Ile Asn Glu
                           100                     105                     110

Leu Val Lys Val Met Gly His Leu Ser Pro Arg Val Thr Leu Arg Lys
                       115                     120                     125

Arg Lys Arg Ser Arg Cys Cys Phe Gly Gly Asn Arg Leu Asn Lys
           130                     135                     140

Asn Asn Pro Ala Ser Thr Ile
          145                 150

<210> SEQ ID NO 17
<211> LENGTH: 133
<212> TYPE: PRT
<213> ORGANISM: Mus sp.

<400> SEQUENCE: 17

His Gly Thr Val Ile Glu Ser Leu Glu Ser Leu Asn Asn Tyr Phe Asn
           1               5                      10                      15

Ser Ser Gly Ile Asp Val Glu Glu Lys Ser Leu Phe Leu Asp Ile Trp
                           20                      25                      30

Arg Asn Trp Gln Lys Asp Gly Asp Met Lys Ile Leu Gln Ser Gln Ile
```

```
                35                  40                  45

Ile Ser Phe Tyr Leu Arg Leu Phe Glu Val Leu Lys Asp Asn Gln Ala
        50                  55                  60

Ile Ser Asn Asn Ile Ser Val Ile Glu Ser His Leu Ile Thr Thr Phe
 65                  70                  75                  80

Phe Ser Asn Ser Lys Ala Lys Lys Asp Ala Phe Met Ser Ile Ala Lys
                85                  90                  95

Phe Glu Val Asn Asn Pro Gln Val Gln Arg Gln Ala Phe Asn Glu Leu
               100                 105                 110

Ile Arg Val Val His Gln Leu Leu Pro Glu Ser Ser Leu Arg Lys Arg
            115                 120                 125

Lys Arg Ser Arg Cys
        130

<210> SEQ ID NO 18
<211> LENGTH: 133
<212> TYPE: PRT
<213> ORGANISM: Rattus sp.

<400> SEQUENCE: 18

Gly Thr Leu Ile Glu Ser Leu Glu Ser Leu Lys Asn Tyr Phe Asn Ser
 1               5                  10                  15

Ser Ser Met Asp Ala Met Glu Gly Lys Ser Leu Leu Leu Asp Ile Trp
                20                  25                  30

Arg Asn Trp Gln Lys Asp Gly Asn Thr Lys Ile Leu Glu Ser Gln Ile
            35                  40                  45

Ile Ser Phe Tyr Leu Arg Leu Phe Glu Val Leu Lys Asp Asn Gln Ala
        50                  55                  60

Ile Ser Asn Asn Ile Ser Val Ile Glu Ser His Leu Ile Thr Asn Phe
 65                  70                  75                  80

Phe Ser Asn Ser Lys Ala Lys Lys Asp Ala Phe Met Ser Ile Ala Lys
                85                  90                  95

Phe Glu Val Asn Asn Pro Gln Ile Gln His Lys Ala Val Asn Glu Leu
               100                 105                 110

Ile Arg Val Ile His Gln Leu Ser Pro Glu Ser Ser Leu Arg Lys Arg
            115                 120                 125

Lys Arg Ser Arg Cys
        130

<210> SEQ ID NO 19
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ac-K(Pam)

<400> SEQUENCE: 19

Xaa Leu Thr Asn Tyr Ser Val Thr Asp Leu Asn Val Gln Arg Lys Ala
 1               5                  10                  15

Ile His Glu Leu Ile Gln Val Met Ala Glu Leu Ser Pro Ala Ala Lys
                20                  25                  30

Thr Gly Lys Arg Lys Arg Ser Gln Met
            35                  40
```

```
<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ac-K(Pam)

<400> SEQUENCE: 20

Xaa Ala Lys Phe Glu Val Asn Asn Pro Gln Val Gln Arg Gln Ala Phe
 1               5                  10                  15

Asn Glu Leu Ile Arg Val Val His Gln Leu Leu Pro Glu Ser Ser Leu
            20                  25                  30

Arg Lys Arg Lys Arg Ser Arg
            35

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ac-K(Pam)

<400> SEQUENCE: 21

Xaa Ile Arg Val Val His Gln Leu Leu Pro Glu Ser Ser Leu Arg Lys
 1               5                  10                  15

Arg Lys Arg Ser Arg
            20

<210> SEQ ID NO 22
<211> LENGTH: 38
<212> TYPE: PRT
<213> ORGANISM: Mus sp.

<400> SEQUENCE: 22

Ala Lys Phe Glu Val Asn Asn Pro Gln Val Gln Arg Gln Ala Phe Asn
 1               5                  10                  15

Glu Leu Ile Arg Val Val His Gln Leu Leu Pro Glu Ser Ser Leu Arg
            20                  25                  30

Lys Arg Lys Arg Ser Arg
            35

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Ser Arg Glu Asn Gln Asn Ala Val Lys Ile Gln Lys Leu Ser Val
 1               5                  10                  15

Val Leu Arg Arg Glu Gln Lys His Arg Val Glu Arg Leu Ala Phe Arg
            20                  25                  30

Asn Gln Ser Leu Pro Phe
            35
```

```
<210> SEQ ID NO 24
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ac-K(Pam)

<400> SEQUENCE: 24

Xaa Pro Ser Arg Glu Asn Gln Asn Ala Val Lys Ile Gln Lys Leu Ser
 1               5                  10                  15

Val Val Leu Arg Arg Glu Gln Lys His Arg Val Glu Arg Leu Ala Phe
            20                  25                  30

Arg Asn Gln Ser Leu Pro Phe
            35

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ac-K(Pam)

<400> SEQUENCE: 25

Xaa Glu Ser Ser Leu Arg Lys Arg Lys Arg Ser Arg
 1               5                  10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Asp Ala Glu Leu Asn Pro Arg Phe
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Glu Leu Asp Leu Glu Lys Gly Leu
 1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
Asp Glu Leu Glu Ala Val Pro Asn Ile
  1               5
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Lys Glu Asp Ala Leu Gln Arg Pro Val
  1               5
```

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Glu Asp Ala Leu Gln Arg Pro Val Ala
  1               5
```

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Gly Glu Lys Leu Arg Val Leu Gly Tyr
  1               5
```

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Glu Asp Thr Met Glu Val Glu Glu Phe
  1               5
```

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Met Glu Tyr Leu Glu Lys Lys Asn Phe
  1               5
```

<210> SEQ ID NO 34
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 34

Asn Glu Glu Ala Ala Asp Glu Val Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Asn Gln Glu Arg Phe Arg Met Ile
 1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Phe Gln Lys Leu Ala Ser Gln Leu
 1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Arg Lys Leu Arg His Val Phe Leu
 1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Leu Lys Ile Lys Ile Ser Gln Ile
 1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Val Lys Leu Gln Thr Val His
 1               5
```

```
<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Ala Leu Gln Arg Pro Val Ala Ser
 1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ala Lys Thr Lys Ala Thr Ser Leu
 1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Gln Gln Met Arg Asn Lys Phe Ala
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Met Arg Asn Lys Phe Ala Phe
 1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Pro Arg Phe Leu Lys Asp Asn Leu
 1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

Thr Pro Asp Cys Ser Ser Asn Glu Asn Leu
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Pro Arg Arg Gln Ser Met Thr Val
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Pro Gly Gln Arg Ser Ile Ser Leu
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Pro Asn Leu Val Gln Leu Leu Gly Val
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Pro Lys Pro Ser Asn Gly Ala Gly Val
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Pro Leu Arg Arg Gln Val Thr Val
1               5

<210> SEQ ID NO 51
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 51

Ser Pro Ala Pro Val Pro Ser Thr Leu
 1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Arg Cys Lys Ala Ser Ile Arg Arg
 1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Gln Arg Trp Gly Phe Phe Arg Arg
 1               5                  10

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Arg Val Gly Asp Leu Phe Gln Lys
 1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Arg Val His Ser Arg Asn Gly Lys
 1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Leu Tyr Lys Pro Val Asp Arg Val
 1               5
```

```
<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Leu Ser Ser Ile Asn Glu Glu Ile
  1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Leu Leu Lys Asp Ser Phe Met Val
  1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Met Val Glu Leu Val Glu Gly Ala
  1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Leu Ser Glu Gln Glu Ser Leu Leu
  1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Leu Thr Asn Ser Cys Val Lys Leu
  1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 62

Gly Leu Tyr Gly Phe Leu Asn Val Ile Val
 1               5                  10

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Leu Asn Val Thr Val His Ser Ala
 1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Leu Leu Tyr Met Ala Thr Gln Ile
 1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Ile Pro Leu Ile Ser Thr Arg Val
 1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Val Leu Asp Ser Thr Glu Ala Leu
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asn Gln Glu Arg Phe Arg Met Ile Tyr
 1               5

<210> SEQ ID NO 68
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 68

Val Gly Asp Ala Ser Arg Pro Pro Tyr
  1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Val Pro Glu Leu Tyr Glu Ile His Lys
  1               5                  10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Leu Ala Ser Gln Leu Gly Val Tyr
  1               5

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Met Val Glu Leu Val Glu Gly Ala Arg Lys
  1               5                  10

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Val His Ser Ala Thr Gly Phe Lys
  1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Thr Gly Phe Lys Gln Ser Ser Lys
  1               5
```

```
<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Lys Gln Ser Ser Lys Ala Leu Gln Arg
  1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Val Tyr Glu Gly Val Trp Lys Lys Tyr
  1               5                  10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Leu Ala Tyr Asn Lys Phe Ser Ile Lys
  1               5                  10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asn Leu Phe Ser Ala Leu Ile Lys Lys
  1               5

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Val Ala Pro Ala Ser Gly Leu Pro His Lys
  1               5                  10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 79

Leu Ile Ser Thr Arg Val Ser Leu Arg Lys
 1               5                  10

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ile Ala Ser Gly Ala Ile Thr Lys
 1               5

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Gln Ser Ser Lys Ala Leu Gln Arg Pro Val Ala Ser
 1               5                  10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Val Glu Gly Asn Leu Ala Arg Val Glu Tyr
 1               5                  10

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ser Asp Cys Thr Thr Ile His Tyr
 1               5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Leu Pro Glu Asn Asn Val Leu Ser Pro Leu
 1               5                  10

<210> SEQ ID NO 85
<211> LENGTH: 9
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Met Pro Glu Ala Ala Pro Pro Val
 1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Met Pro Glu Ala Ala Pro Arg Val
 1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Leu Asn Lys Met Phe Cys Gln Leu
 1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Thr Pro Pro Pro Gly Thr Arg Val
 1               5

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Leu Ala Pro Pro Gln His Leu Ile Arg Val
 1               5                   10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Leu Gly Arg Asn Ser Phe Glu Val

```
<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Leu Asp Gly Glu Tyr Phe Thr Leu
 1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Val Arg Ala Met Ala Ile Tyr Lys
 1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Arg Thr Glu Glu Glu Asn Leu Arg
 1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Leu Pro Pro Gly Ser Thr Lys Arg
 1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Pro Glu Asn Asn Val Leu Ser Pro Leu
 1               5                  10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 96

Ala Pro Arg Met Pro Glu Ala Ala Pro Pro Val
 1               5                  10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Pro Arg Met Pro Glu Ala Ala Pro Arg Val
 1               5                  10

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Pro Pro Gln His Leu Ile Arg Val
 1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Pro Ile Leu Thr Ile Ile Thr Leu
 1               5

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Pro Leu Asp Gly Glu Thr Tyr Phe Thr Leu
 1               5                  10

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Gln Leu Ala Lys Thr Cys Pro Val
 1               5

<210> SEQ ID NO 102

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Leu Ala Pro Pro Gln His Leu Ile
  1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Thr Phe Arg His Ser Val Val Val
  1               5

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Leu Pro Glu Asn Asn Val Leu Ser Pro Leu
  1               5                  10

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Met Pro Glu Ala Ala Pro Pro Val
  1               5

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Leu Ile Arg Val Glu Gly Asn Leu Arg Val
  1               5                  10

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107
```

Met Leu Leu Ala Val Leu Tyr Cys Leu
 1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Met Asn Gly Thr Met Ser Gln Val
 1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Tyr Met Asp Gly Thr Met Ser Gln Val
 1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Phe Leu Pro Trp His Arg Leu Phe
 1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ser Glu Ile Trp Arg Asp Ile Asp Phe
 1               5

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Asn Ile Leu Leu Ser Asn Ala Pro Leu Gly Pro Gln Phe Pro
 1               5                  10                  15

<210> SEQ ID NO 113
<211> LENGTH: 13
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 113

Ser Tyr Leu Gln Asp Ser Asp Pro Asp Ser Phe Gln Asp
  1               5                  10

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Lys Thr Trp Gly Gln Tyr Trp Gln Val
  1               5

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Met Leu Gly Thr His Thr Met Glu Val
  1               5                  10

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Met Leu Gly Thr His Thr Met Glu Val
  1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ile Thr Asp Gln Val Pro Phe Ser Val
  1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Tyr Leu Glu Pro Gly Pro Val Thr Ala
  1               5
```

```
<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Leu Leu Asp Gly Thr Ala Thr Leu Arg Leu
  1               5                  10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Val Leu Tyr Arg Tyr Gly Ser Phe Ser Val
  1               5                  10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Leu Ala Asp Thr Asn Ser Leu Ala Val
  1               5                  10

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Leu Leu Ala Val Gly Ala Thr Lys
  1               5

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: This position may or may not be present

<400> SEQUENCE: 123

Glu Ala Ala Gly Ile Gly Ile Leu Thr Val
  1               5                  10

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 124

Ile Leu Thr Val Ile Leu Gly Val Leu
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Met Ser Leu Gln Arg Gln Phe Leu Arg
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Leu Gly Pro Gly Arg Pro Tyr Arg
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Glu Lys Leu Ile Val Val Leu Phe
1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Cys Asp Pro His Ser Gly His Phe Val
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Tyr Leu Asp Ser Gly Ile His Phe
1               5

<210> SEQ ID NO 130

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Phe Pro Ser Asp Ser Trp Cys Tyr Phe
  1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Ala Asp Pro Thr Gly His Ser Tyr
  1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Ala Tyr Gly Glu Pro Arg Lys Leu
  1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Val Asp Pro Ile Gly His Leu Tyr
  1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Phe Leu Trp Gly Pro Arg Ala Leu Val
  1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135
```

Met Glu Val Asp Pro Ile Gly His Leu Tyr
1               5                   10

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Ala Arg Ala Val Phe Leu Ala Leu
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Tyr Arg Pro Arg Pro Arg Arg Tyr
1               5

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Pro Ser Ser Asn Arg Ile Arg Asn Thr
1               5                   10

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Val Leu Pro Asp Val Phe Ile Arg Cys
1               5

<210> SEQ ID NO 140
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Pro Asp Thr Arg Pro Ala Pro Gly Ser Thr Ala Pro Pro Ala His Gly
1               5                   10                  15

Val Thr Ser Ala
            20

<210> SEQ ID NO 141
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Leu Glu Gly Leu Ile His Ser Gln Arg Arg
 1               5                  10

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Pro Asp Trp Gln Asn Tyr Thr
 1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Leu Thr Phe Gly Trp Cys Tyr Lys Leu
 1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Arg Phe Asp Ser Arg Leu Ala Phe
 1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Arg Glu Leu His Pro Glu Tyr
 1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Lys Leu Thr Pro Leu Cys Val Thr Leu
```

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Leu Tyr Asn Thr Val Ala Thr Leu
 1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Leu Val Glu Ile Cys Thr Glu Met
 1               5

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Val Leu Asp Val Gly Asp Ala Tyr Phe Ser Val
 1               5                   10

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Lys Ile Tyr Gln Tyr Met Asp Asp Leu
 1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Lys Ile Glu Glu Leu Arg Gln His Leu
 1               5

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Leu Leu Arg Trp Gly Leu Thr Thr Pro Asp Lys
 1               5                  10

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Leu Lys Glu Pro Val His Gly Val
 1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Pro Leu Val Lys Leu Trp Tyr Gln Leu
 1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Glu Leu Val Asn Gln Asp Glu Gln Leu
 1               5

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Leu Thr Phe Gly Trp Cys Phe Lys Leu
 1               5                  10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Val Leu Gln Trp Arg Phe Asp Ser Arg Leu
 1               5                  10

<210> SEQ ID NO 158

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Leu His His Val Ala Arg Glu Leu
 1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Leu Leu Asn Ala Thr Val Asp Ile
 1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asp Leu Asn Thr Met Leu Asn Thr Val
 1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Val Ile Tyr Gln Tyr Met Asp Asp Leu
 1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Pro Leu Val Lys Leu Trp Tyr Gln Leu
 1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163
```

```
Val Leu Val Gly Pro Thr Pro Val Asn Ile
 1               5                   10
```

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

```
Thr Val Tyr Tyr Gly Val Pro Val
 1               5
```

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

```
Ser Leu Lys Pro Cys Val Lys Leu
 1               5
```

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

```
Arg Ile Gln Arg Gly Pro Gly Arg Ala
 1               5
```

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

```
Thr Leu Thr Ser Cys Asn Thr Ser Val
 1               5
```

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

```
Phe Ile Asn Met Trp Gln Glu Val
 1               5
```

<210> SEQ ID NO 169
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 169

Val Val Gln Gly Ala Tyr Arg Ala Ile
 1               5

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

His Ala Gly Pro Ile Ala Pro Gly Gln Met
 1               5                  10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gln Met Lys Asp Cys Thr Glu Arg Gln Ala
 1               5                  10

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Phe Leu Gln Ser Arg Pro Glu Thr Ala
 1               5

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Glu Ser Glu Leu Val Asn Gln Ile Ile Glu Gly
 1               5                  10

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Ile Arg Leu Arg Pro Gly Gly Lys
 1               5
```

```
<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Leu Arg Pro Gly Gly Lys Lys Lys
 1               5

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Leu Val Glu Ile Cys Thr Glu Met Glu Lys
 1               5                  10

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Ile Phe Gln Ser Ser Met Thr Lys
 1               5

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Leu Glu Ile Gly Gln His Arg Thr Lys
 1               5                  10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gln Val Pro Leu Arg Pro Met Thr Tyr Lys
 1               5                  10

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180
```

Thr Val Tyr Tyr Gly Val Pro Val Trp Lys
1               5                  10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Arg Leu Arg Asp Leu Leu Ile Val Thr Arg
1               5                  10

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Lys Ile Arg Leu Arg Pro Gly Gly Lys
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Ile Phe Gln Ser Ser Met Thr Lys
1               5

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln Ile Tyr Gln Glu Pro Phe Lys Asn Leu Lys
1               5                  10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gln Val Pro Leu Arg Pro Met Thr Tyr Lys
1               5                  10

<210> SEQ ID NO 186
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 186

Ala Val Asp Leu Ser His Phe Leu Lys
 1               5

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Cys Gln Val Gly Gly Pro Gly His Lys
 1               5                  10

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Thr Leu Tyr Cys Val His Gln Arg
 1               5

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Leu Phe Cys Ala Ser Asp Ala Lys Ala Tyr
 1               5                  10

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Tyr Leu Lys Asp Gln Gln Leu Leu
 1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Tyr Leu Lys Asp Gln Gln Leu Leu
 1               5
```

```
<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Val Tyr Tyr Asp Pro Ser Lys Asp Leu
  1               5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ile Tyr Gln Glu Pro Phe Lys Asn Leu
  1               5

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Ser Glu Leu Val Asn Gln Ile Ile Glu Gly
  1               5                  10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Glu Thr Ile Asn Glu Glu Ala Ala Glu Trp
  1               5                  10

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Val Ile Pro Met Phe Ser Ala Leu
  1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 197

Arg Ala Ile Arg His Ile Pro Arg Arg
 1               5

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Arg Leu Arg Asp Leu Leu Leu Ile Val Thr Arg
 1               5                  10

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Ile Lys Gln Ile Ile Asn Met Trp
 1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

His Arg Leu Arg Asp Leu Leu Leu Ile
 1               5

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Pro Ile Gln Lys Glu Thr Trp Glu Thr Trp
 1               5                  10

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ile Ile Leu Gly Leu Asn Lys Ile Val Arg
 1               5                  10

<210> SEQ ID NO 203
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 203

Tyr Leu Ala Trp Val Pro Ala His Lys
 1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Phe Pro Val Thr Gln Val Pro Leu Arg
 1               5

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Thr Pro Gly Pro Gly Val Arg Tyr Pro Leu
 1               5                  10

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Arg Pro Asn Asn Asn Thr Arg Lys Ser Ile
 1               5                  10

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile Pro Arg Arg Ile Arg Gln Gly Leu
 1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Tyr Leu Ala Trp Val Pro Ala His Lys
 1               5
```

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Arg Val Lys Glu Lys Tyr Gln His Leu
 1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Gly Lys Lys Lys Tyr Lys Leu Lys
 1               5

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Phe Leu Lys Glu Lys Gly Gly Leu
 1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Glu Ile Tyr Lys Arg Trp Ile Ile
 1               5

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Tyr Leu Lys Asp Gln Gln Leu Leu
 1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 214

Pro Arg Arg Ile Arg Gln Gly Leu
 1               5

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Arg Ile Arg Gln Gly Leu Glu Arg Ile Leu
 1               5                  10

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Asp Cys Lys Thr Ile Leu Lys Ala Leu
 1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Pro Lys Val Lys Gln Trp Pro Leu
 1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Glu Trp Arg Phe Asp Asp Ser Arg Leu
 1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Glu Arg Tyr Leu Lys Asp Gln Gln Leu
 1               5

<210> SEQ ID NO 220
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asp Arg Phe Tyr Lys Thr Leu Arg Ala
  1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asp Leu Asn Thr Met Leu Asn Thr Val
  1               5

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Leu Arg Ala Glu Gln Ala Ser Val Gln Glu Val
  1               5                  10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Arg Ala Glu Gln Ala Ser Val Gln Glu Val
  1               5                  10

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Tyr Pro Leu Thr Phe Gly Trp Cys Tyr
  1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Tyr Pro Leu Thr Phe Gly Trp Cys Phe
```

```
<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Lys Arg Trp Ile Ile Leu Gly Leu Asn Lys
 1               5                  10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gln Val Pro Leu Arg Pro Met Thr Tyr Lys
 1               5                  10

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Arg Tyr Pro Leu Thr Phe Gly Trp
 1               5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Tyr Pro Leu Thr Phe Gly Trp
 1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Glu Arg Tyr Leu Lys Asp Gln Gln Leu
 1               5

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 231

Gly Arg Arg Gly Trp Glu Ala Leu Lys Tyr
 1               5                  10

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Asp Pro Asn Pro Gln Glu Val Val Leu
 1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Arg Pro Val Val Ser Thr Gln Leu Leu
 1               5

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Val Pro Leu Asp Lys Asp Phe Arg Lys Tyr
 1               5                  10

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Pro Ala Ile Phe Gln Ser Ser Met
 1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Asn Pro Asp Ile Val Ile Tyr Gln Tyr
 1               5

<210> SEQ ID NO 237

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ile Pro Leu Thr Glu Glu Ala Glu Leu
  1               5

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Glu Pro Ile Val Gly Ala Glu Thr Phe Tyr
  1               5                  10

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Phe Pro Val Arg Pro Gln Val Pro Leu
  1               5

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Val Pro Leu Arg Pro Met Thr Tyr
  1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Thr Ala Val Pro Trp Asn Ala Ser Trp
  1               5

<210> SEQ ID NO 242
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242
```

```
Val Pro Val Trp Lys Glu Ala Thr Thr Thr Leu
 1               5                  10
```

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

```
Asn Ser Ser Gln Val Ser Gln Asn Tyr
 1               5
```

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Pro Pro Ile Pro Val Gly Glu Ile Tyr
 1               5
```

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

```
Tyr Phe Pro Asp Trp Gln Asn Tyr Thr
 1               5
```

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

```
Ser Glu Gly Ala Thr Pro Gln Asp Leu
 1               5
```

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

```
Leu Glu Ser Gly Ala Thr Pro Gln Asp Leu
 1               5                  10
```

<210> SEQ ID NO 248
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 248

Arg Ala Ile Glu Ala Gln Gln His Leu
 1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Leu Val Glu Ile Cys Thr Glu Met
 1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Lys Glu Gly Lys Ile Ser Lys Ile
 1               5

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Thr Ala Phe Thr Ile Pro Ser Ile
 1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Phe His His Val Ala Arg Glu Leu
 1               5

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Val Pro Val Trp Lys Glu Ala Thr Thr Thr Leu
 1               5                  10
```

```
<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Thr Ser Leu Thr Gln Glu Gln Ile Gly Trp
  1               5                  10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

His Thr Gln Gly Tyr Phe Pro Asp Trp Gln
  1               5                  10

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

His Thr Gln Gly Tyr Phe Pro Asp Trp
  1               5

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Tyr Phe Pro Asp Trp Gln Asn
  1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ile Ser Pro Arg Thr Leu Asn Ala Trp
  1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259
```

-continued

```
Phe Ser Pro Glu Val Ile Pro Met Phe
  1               5
```

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

```
Arg Leu Arg Pro Gly Gly Lys Lys Lys Tyr
  1               5                  10
```

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

```
Leu Gly Leu Asn Lys Ile Val Arg Met Tyr
  1               5                  10
```

<210> SEQ ID NO 262
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

```
Leu Val Gly Lys Leu Asn Trp Ala Ser Gln Ile Tyr
  1               5                  10
```

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

```
Ala Val Asp Leu Ser His Phe Leu
  1               5
```

<210> SEQ ID NO 264
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

```
Thr Gln Gly Tyr Phe Pro Asp Trp Gln Asn Tyr
  1               5                  10
```

<210> SEQ ID NO 265
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 265

Ser Phe Asn Cys Gly Gly Glu Phe Phe
 1               5

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Val Thr Asp Ser Gln Tyr Ala Leu Gly Ile
 1               5                   10

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Arg Ala Glu Gln Ala Ser Gln Glu Val
 1               5

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Lys Ala Ala Leu Asp Leu Ser His Pro Leu
 1               5                   10

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gln Ala Thr Gln Glu Val Lys Asn Trp
 1               5

<210> SEQ ID NO 270
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Tyr Met Leu Asp Leu Gln Pro Glu Thr Thr
 1               5                   10
```

```
<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Leu Leu Met Gly Thr Leu Gly Ile Val
  1               5

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Thr Leu Gly Ile Val Cys Pro Ile
  1               5

<210> SEQ ID NO 273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Thr Ile His Asp Ile Ile Leu Glu Cys Val
  1               5                  10

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Lys Leu Pro Gln Leu Cys Thr Glu Leu
  1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Arg Pro Pro Lys Leu Pro Gln Leu
  1               5

<210> SEQ ID NO 276
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 276

Leu Arg Arg Glu Val Tyr Asp Phe Ala Phe Arg Asp Leu Cys Ile Val
1               5                   10                  15

Tyr Arg Asp Gly Asn Pro Tyr
            20

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ile Ser Glu Tyr Arg His Tyr Cys Tyr
1               5

<210> SEQ ID NO 278
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Glu Lys Gln Arg His Leu Asp Lys Lys Gln Arg Phe His Asn Ile Arg
1               5                   10                  15

Gly Arg Trp Thr
            20

<210> SEQ ID NO 279
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Gln Ala Glu Pro Asp Arg Ala His Tyr Asn Ile Val Thr Phe
1               5                   10                  15

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gln Ala Glu Pro Asp Arg Ala His Tyr
1               5

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 281

```
Glu Pro Asp Arg Ala His Tyr Asn Ile Val
  1               5                  10
```

LIPOPEPTIDES CONTAINING AN INTERFERON-γ FRAGMENT, AND USES THEREOF IN PHARMACEUTICAL COMPOSITIONS This application is 371 of PCT/FR 99/00259 filed Feb. 5, 1999.

The present invention relates to lipopeptides containing an interferon-γ fragment, as well as to their use in particular as medicinal products in the context of treating or preventing pathologies against which interferon-γ is liable to have activity by means of at least one of its biological effects, or as an immunity adjuvant which can be used in a vaccine composition for stimulating, orienting or re-orienting the balance of the immune response with respect to any antigen, in particular by promoting the establishment of a type-1 immune response relative to a type-2 response with respect to this antigen.

Cytokines, which are cell immunity components, are classified in two groups: type-1 and type-2 cytokines characterized, respectively, by IL-2, IL-12, interferon-gamma (IFN-γ), IL-4 and IL-5. These two groups regulate and control themselves mutually. They are closely linked to the induction and regulation of the immune response.

The expression "type-1 immune response" means the induction of a type-1 cytokine profile.

The expression "type-2 immune response" means the induction of a type-2 cytokine profile.

On account of its pleiotropic activities, IFN-γ plays a fundamental role in establishing the immune balance. Specifically, this cytokine is involved in various immune defence processes, in particular against viruses, bacteria and protozoan parasites. Furthermore, it inhibits type-2 cytokines and promotes the establishment of a type-1 response which is quite often required to combat certain tumours, and to combat viral and parasitic infections.

Consequently, a therapeutic strategy involving this cytokine appears attractive, but comes up against certain difficulties. These difficulties are the consequences of the short lifetime of IFN-γ, imposing repeated injections of large doses, this often being associated with side effects due to the broad spectrum of activity of the molecule.

The production of recombinant human IFN-γ and its use in human therapy also comes up against the instability of the molecule, which is highly dependent upon the state of glycosylation of the molecule (Saraneva et al., 1995), which is very difficult or impossible to obtain with the expression systems used.

IFN-γ is a glycoprotein of 133 to 143 amino acids depending on the species, which is active in the homodimer form. It acts on the target cells by stimulating a transmembrane receptor, doing so while respecting a species barrier. This species specificity is based on the specific recognition between the outer (or extracellular) portion of the IFN-γ receptor and the N-terminal portion of the cytokine.

The association of IFN-γ and its receptor leads to a dimerization of this receptor and regulates the cytoplasmic association of tyrosine Janus kinase 2 (JAK 2) with the alpha chain of the receptor. This results in a trans- and/or an autophosphorylation of JAK 1 and JAK 2. This represents the first steps in the activation cascade of the transduction pathway of the signal associated with the stimulation by this cytokine, resulting in biological activities such as the induction of the expression of class II CMH molecules, Fc-γ receptors, and adhesion molecules such as VCAM-1.

However, a biological activity independent of the species barrier is observed when the cytokine is delivered inside target cells (in liposomes (Fidler et al., 1985)), or introduced by micro-injection (Smith et al., 1990), or transfection (Sanceau et al., 1987). These results appeared to suggest the existence of an intracellular activation pathway.

This second activation pathway quite probably takes place after interaction of the C-terminal portion of IFN-γ (sequence 95–133 in the case of murine IFN-γ), with the alpha chain of the IFN-γ receptor. This sequence has a binding site which is independent of the species, located at the level of residues 253–287 of the alpha chain of the murine IFN-γ receptor which is of strong affinity (Szente and Johnson, 1994). This intracytoplasmic binding site is located close to the cell membrane and to the JAK 2 tyrosine kinase binding site. This second recognition step appears to be essential to the biological function of this cytokine: the interaction of the C-terminal peptides of IFN-γ with the cytoplasmic portion of the IFN-γ receptor increases the binding of JAK 2 with the alpha chain of the receptor (Szente et al., 1995), which results in an activation of the signal transduction pathway.

These observations supported and explained previous observations regarding the capacity to activate the IFN-γ receptor of murine macrophages with vectorized human IFN-γ. The probable physiological mechanism of action of IFN-γ is thus thought to involve an internalization of the complex formed between IFN-γ and its receptor, following the first recognition step.

Another mechanism may be envisaged, which is thought to correspond to an intracrine stimulation, in the course of which the IFN-γ-producing cells would be autostimulated by the IFN-γ produced inside the cell, without an autocrine activity being necessary via the extracellular portion of the cytokine receptor.

In vitro, the treatment of phagocytic cells of the murine P388D1 cell line (macrophage monocytes) with murine (sequence 95–133) or human (sequence 95–134) IFN-γ peptides for 24 hours at high concentration (100 μM) can induce expression of the class II CMH receptor. The high concentration required can be explained by the low degree of penetration of the peptide across the cell membrane (by means of pinocytosis activity of the cell studied), or by an inadequate conformation of the peptide, or by a combination of the two phenomena (Szente.et al., 1994).

More recently, Szente identified the structural elements involved in the agonist activity of the C-terminal peptide, and observed that an α helix comprising the unit RKRKR is essential for binding to the cytoplasmic domain of the IFN-γ receptor and for inducing the biological activity (Szente et al., 1996).

Only phagocytic cells have a relative sensitivity to the C-terminal peptide of IFN-γ as used by Szente. These observations are of fundamental interest since they have made it possible to support the hypothesis of the intracrine activity of this cytokine, but they do not propose a product which can be used as such: the biological activity observed with the unmodified peptide moreover did not have the complete spectrum of activity of IFN-γ. In particular, Szente did not obtain induction of the antiviral activity considered as the signature of the IFN-γ activity, and which is used to assay the activity of production batches of this cytokine, since the cells used to carry out the standard test have no phagocytic activity.

The therapeutic use of peptides corresponding to the C-terminal portion of mammalian IFN-γ, such as the above-mentioned murine peptide 95–133 or human peptide 95–134, would be particularly advantageous since it would allow an induction of the biological activity observed in the case of using the whole IFN-γ, by direct binding of the said peptide to the IFN-γ intracellular receptor, without passing via the intermediate step of recognition of the extracellular receptor of this IFN-γ, while at the same time respecting a physiological mechanism of activation if reference is made to an intracrine activity, and thus capable of exhibiting a complete agonist nature.

Specifically, as has been seen above, whole IFN-γ binds first to an extracellular receptor which is specific to a given species. Next, the IFN-γ appears to be internalized inside the cell, and might react with the intracellular portion of the said receptor, which, as has been mentioned above, does not appear to be specific to a given species.

Consequently, the use of the above-mentioned peptides corresponding to the C-terminal portion of mammalian IFN-γ would make it possible to solve this species-barrier problem, and thus to use a peptide corresponding to the C-terminal portion of the IFN-γ of a given mammal, in the context of treating all mammals. Furthermore, the direct cellular internalization of these peptides, thus avoiding the step of recognizing the extracellular receptor, would have the advantage of limiting the residence time of the peptide outside the cells, and thus of contributing towards limiting the risks of degradation of this peptide.

However, as has been seen above, the low degree of penetration of the above-mentioned murine IFN-γ peptide 95–133 observed in vitro in macrophages does not make it possible to envisage a therapeutic use of the above-mentioned peptides, since the main target cells of these peptides, in particular including the antigen-presenting cells, or the cytotoxic or helper T cells, have at best only a pinocytosis activity, of which it may be deduced, from the above-mentioned 1994 article by Szente et al., that it is insufficient for rapid and efficient internalization of the said peptide.

The possibility of vectorizing peptides inside living cells by modifying them with a lipid chain has already been the subject of studies. The comparison of a series of lipopeptides derived from a pseudosubstrate sequence of protein kinase C allowed the Inventors to demonstrate that the modification of peptides with an N- or C-terminal palmitoyl-lysine group leads to the production of a vector which is efficient in terms of cytoplasmic addressing (Loing et al., 1996). Modification with a palmitoyl-lysine allows a rapid passage of peptides of 9 to 17 residues inside living cells, which can be observed indirectly by measuring the biological activity (Thiam et al., 1997) or indirectly by means of experiments performed by optical, confocal or electron microscopy.

The present invention derives from the demonstration by the inventors of the fact that lipopeptides containing the above-mentioned peptides corresponding to the C-terminal portion of mammalian IFN-γ allows the said peptides to penetrate into cells, independently of a phagocytic activity, while at the same time conserving their biological activity. The experiments carried out by the Inventors have proved that it was impossible to observe this biological activity on non-phagocytic cells, when the above-mentioned peptide 95–133 is used at the same doses as the lipopeptide comprising this peptide 95–133. It was impossible to predict, firstly, that combining a simple lipid chain with such a large peptide (which is markedly larger in size than those described above in the article by Thiam et al., 1997) would allow this peptide to cross the cell membrane, and, secondly, that this lipid chain would not prevent, in particular by means of a masking phenomenon, the binding of the said peptides to the intracellular portion of mammalian IFN-γ receptors.

The main object of the present invention is thus to provide novel lipopeptide compounds allowing an efficient penetration of peptides corresponding to the C-terminal portion of mammalian IFN-γ into the target cells of IFN-γ.

In this respect, the present invention makes it possible to provide compounds that are agonists of the total or partial activity of IFN-γ (i.e. compounds which mimic at least one of the biological or pharmacological activities of IFN-γ), and whose activity was demonstrated in vivo for the first time by the Inventors on animals, the said compounds being able to be used in human or animal therapy.

A further object of the present invention is to provide novel laboratory reagents, as well as novel pharmaceutical compositions, comprising the above-mentioned lipopeptides.

A further object of the invention is to provide novel pharmaceutical compositions having the advantage over recombinant IFN-γ of exhibiting fewer side effects than the latter, in particular since the number of times the said pharmaceutical compositions are taken is markedly smaller than that for IFN-γ, and since the delay of action of these compositions is much shorter than that for IFN-γ.

Furthermore, the pharmaceutical compositions of the invention have the advantage of being able to be stored for markedly longer periods than recombinant IFN-γ, and of allowing this under markedly less restrictive conditions since there is nothing to fear from a sporadic breakdown of their refrigeration conditions and they can thus, in this respect, be stored at ambient temperature.

The invention relates to any lipopeptide which is characterized in that it comprises:

- a peptide portion capable of binding to the intracellular portion of the IFN-γ receptors, but which cannot bind to the extracellular portion of the said receptors, the said peptide portion comprising:
  - the peptide sequence consisting of from about 30 to about 50 of the last contiguous amino acids of the C-terminal end of mammalian interferon-γ (IFN-γ), of which, where appropriate, the last 3 to 20 amino acids have been suppressed,
  - or any fragment, in particular of from about 5 to about 30 amino acids, of the above-mentioned peptide sequence of the C-terminal end of mammalian IFN-γ,
  - or any peptide sequence derived from the above-mentioned peptide sequence of the C-terminal end of IFN-γ, or of an above-mentioned fragment,
- and one or more lipophilic portions, advantageously chosen from those comprising:
  - a linear or branched, saturated or unsaturated C4 to C20 hydrocarbon-based chain,
  - or a steroid group, where appropriate linked to the above-mentioned hydrocarbon-based chain,
- the said lipophilic portions optionally being combined with a short vector peptide (in order thus to form vector lipopeptide units) comprising one or more functions that are ionized at physiological pH, and a function for covalently bonding the said hydrocarbon-based chain and/or the said steroid group.

In the text hereinabove and hereinbelow, the expression "lipophilic portion" means any water-insoluble lipophilic molecule which, when bound to the peptide portion defined above, allows a passive intracellular passage of the lipopeptide obtained, by virtue of the hydrophobic properties of the said molecule. The lipopeptide resulting from the binding of the lipophilic portion to the peptide portion is advantageously water-soluble.

The hydrocarbon-based chain of the lipophilic portions is preferably chosen from those of:
palmitic acid,
oleic acid,
linoleic acid,
linolenic acid.

Preferably also, the steroid group of the lipophilic portion (s) is chosen from cholesterol derivatives such as cholest-5-enyl-3-oxyacetic acid or cholest-5-enyl-3-oxycarbonic acid.

The invention relates, more particularly, to any lipopeptide as described above which is characterized in that the lipophilic portion(s) is (are) covalently bonded to one or more amino acids of the peptide portion.

It is advantageous if the Lipohile portion(s) (is) are bonded covalently to the $\alpha NH_2$ or $\epsilon NH_2$ function of a lysine located at the N-terminal or C-terminal position of the peptide portion, or to the thiol function of a cysteine, or to any amino, alcohol or thiol function optionally added to the peptide with a simple spacer.

In this respect, the invention relates, more particularly, to any lipopeptide as defined above in which the lipophilic portion(s) is (are) represented by an $N^\alpha$-acetyl-Lysine $N^\epsilon$(palmitoyl) group (also denoted by the abbreviation Ac-K (Pam)).

The present invention also relates to lipopeptides resulting from a covalent association between a vector lipopeptide unit, as defined above, which ensures vectorization across a cell membrane, and a functional unit derived from one of the above-mentioned mammalian IFN-γ sequences. The vector lipopeptide unit preferably corresponds to a short sequence comprising functions that are ionized at physiological pH (Arg, Lys, Asp or Glu), and a lipid (or lipophilic) portion as described above. The covalent association between the vector lipopeptide unit and the functional unit can be an amide bond, or a non-peptide bond resulting from a simple chemical ligation, obtained by virtue of the reactivity of the thiol (thio ether, thio ester or disulphide) function or of an aldehyde function with a weak base (thiazolidine, oxime, hydrazone). Examples of such ligations, which are conventional to those skilled in the art, are described in the review by Tam and Spetzler, 1995.

By the definition given above of the peptide portion of the lipopeptides of the invention, that is to say "the peptide sequence consisting of from about 30 to about 50 of the last contiguous amino acids of the C-terminal end of mammalian interferon-γ (IFN-γ), of which, where appropriate, the last 3 to 20 amino acids have been suppressed", this means any peptide sequence consisting of from about 30 to about 50 of the last contiguous amino acids of the C-terminal end of mammalian IFN-γ, as well as any peptide sequence consisting of from about 30 to about 50 of the last contiguous amino acids of the C-terminal end of mammalian IFN-γ fragments, these fragments corresponding to the various types of mammalian IFN-γ of which the last 3 to 20 amino acids have been suppressed.

The above-mentioned peptide sequence consisting of from about 30 to about 50 of the last contiguous amino acids of the C-terminal end of mammalian IFN-γ (also denoted hereinbelow as the sequence corresponding to the IFN-γ C-terminal portion), as well as the above-mentioned fragments and sequences derived from this sequence, advantageously contain a sequence of the type XKRYR in which X represents R, G, I, F or K, and Y represents K or R.

Advantageously also, the said peptide sequence corresponding to the IFN-γ C-terminal portion, as well as the above-mentioned fragments and sequences derived from this sequence, specifically recognize the intracellular portion of mammalian IFN-γ receptors and, in this respect, have at least one of the biological and pharmacological properties of mammalian IFN-γ, and are referred to as being agonists of the total or partial activity of mammalian IFN-γ.

By way of illustration, the peptide sequences corresponding to the IFN-γ C-terminal portion, in the above-mentioned lipopeptides, or the fragments of these sequences, or the sequences derived from these sequences or fragments, are further characterized in that they specifically recognize:

the intracellular portion of the human IFN-γ receptor delimited by the amino acids located in positions 252 and 291 of the peptide sequence of the said receptor, or any intracellular portion of the IFN-γ receptors of mammals other than man, in particular the intracellular portion of the murine IFN-γ receptor delimited by the amino acids located in positions 253 and 287 of the peptide sequence of the said receptor.

As has been mentioned above, the peptide portion of the above-mentioned lipopeptides of the invention does not recognize the extracellular portion of the mammalian IFN-γ receptor with IFN-γ.

In this respect, the said peptide portion of the lipopeptides of the invention is such that, when it contains the N-terminal end of mammalian IFN-γ, at least one of the first 20 amino acids of this N-terminal end is suppressed or substituted with a natural or non-natural amino acid, such that the said N-terminal end thus modified is incapable of recognizing and binding to the extracellular IFN-γ receptor.

The peptide portion of the above-mentioned lipopeptides of the invention advantageously does not comprise the N-terminal end of mammalian IFN-γ, which is required for the specific recognition of the extracellular portion of the mammalian IFN-γ receptor with IFN-γ.

The peptide portion of the above-mentioned lipopeptides of the invention is preferably such that it does not comprise the sequence delimited, on the one hand, by the amino acid located in position 1, and, on the other hand, by the amino acid located in position 14 of the peptide sequences of mammalian IFN-γ (in particular of the IFN-γ peptide sequences indicated below).

The invention relates, more particularly, to any lipopeptide as defined above which is characterized in that the peptide portion comprises at least one of the following peptide sequences:

the sequence delimited by the amino acids located in positions 95 and 134:

of the following human IFN-γ peptide sequence:
SEQ ID NO: 2 of the following bovine IFN-γ peptide sequence:
SEQ ID NO: 3 of the following IFN-γ peptide sequence from the monkey *Callithrix jacchus:*
SEQ ID NO: 4 of the following IFN-γ peptide sequence from the monkey *Cercocebus torquatius atys:*
SEQ ID NO: 5 of the following dog IFN-γ peptide sequence:
SEQ ID NO: 6 of the following cat IFN-γ peptide sequence:
SEQ ID NO: 7 of the following deer IFN-γ peptide sequence:
SEQ ID NO: 8 of the following chicken IFN-γ peptide sequence:
SEQ ID NO: 9 of the following horse IFN-γ peptide sequence:
SEQ ID NO: 10 of the following macaque IFN-γ peptide sequence:
SEQ ID NO: 11
of the following pig IFN-γ peptide sequence:
SEQ ID NO: 12
of the following rabbit IFN-γ peptide sequence:
SEQ ID NO: 13
of the following sheep IFN-γ peptide sequence:
SEQ ID NO: 14
of the following marmot IFN-γ peptide sequence:
SEQ ID NO: 15
of the following IFN-γ peptide sequence of *Meriones unguiculatus*:
SEQ ID NO: 16
the sequence delimited by the amino acids located in positions 95 and 133 or 132:
of the following murine IFN-γ peptide sequence:
SEQ ID NO: 17
of the following rat IFN-γ peptide sequence:
SEQ ID NO: 18
the sequence delimited on the N-terminal side by an amino acid located at one of positions 113 to 121, and on the C-terminal side by the amino acid located in position 132 of the murine IFN-γ peptide sequence represented above.

The invention also relates to any lipopeptide as defined above which is characterized in that the COOH function of the C-terminal amino acid is substituted with a group which is resistant to the organism's exopeptidases, in particular with a carboxamide group.

The invention relates, more particularly, to any lipopeptide as defined above, the peptide sequence of which is that:
delimited by the amino acids located in positions 95 and 134 of the human IFN-γ peptide sequence represented above,
or delimited by the amino acids located in positions 95 and 133 or 132 of the murine IFN-γ peptide sequence represented above,
or delimited on the N-terminal side by an amino acid located in one of positions 113 to 121, and on the C-terminal side by the amino acid located in position 132, of the murine IFN-γ peptide sequence represented above, and more particularly that delimited by the amino acids located in positions 113 and 132 of the said IFN-γ peptide sequence,
the COOH function of the C-terminal amino acid of the above-mentioned peptide sequences being, where appropriate, substituted with a group which is resistant to the organism's exopeptidases, in particular with a carboxamide group.

Lipopeptides that are preferred in the context of the present invention are the following:
the lipopeptide whose sequence is delimited by the amino acids located in positions 95 and 134 of the human IFN-γ peptide sequence represented above, corresponding to the following formula:
SEQ ID NO 19
the lipopeptide whose sequence is delimited by the amino acids located in positions 95 and 132 of the murine IFN-γ peptide sequence represented above, corresponding to the following formula:
SEQ ID NO 20
the lipopeptide whose sequence is delimited by the amino acids located in positions 113 and 132 of the murine IFN-γ peptide sequence represented above, corresponding to the following formula:
SEQ ID NO 21.

The expression "peptide sequence derived from the above-mentioned peptide sequence of the C-terminal end of IFN-γ, or of a fragment of the latter", in the context of the lipopeptides of the invention, means any sequence derived:
by substitution and/or suppression and/or addition of one or more amino acids, of the above-mentioned sequence or fragment, and/or
by modification of at least one peptide linkage —CO—NH— of the peptide chain, of the above-mentioned sequence or fragment, in particular by introducing a linkage of the retro or retro-inverso type, and/or
by substitution of at least one amino acid of the peptide chain of the above-mentioned sequence or fragment, with a non-protein-generating amino acid,
the said derived sequence specifically recognizing the intracellular portion of the mammalian IFN-γ receptors and, in this respect, having at least one of the biological or pharmacological properties of mammalian IFN-γ, in particular at least one of the properties listed above.

The expression "sequence derived by introducing a retro-inverso linkage" should be understood as meaning any peptide analogue of the above-mentioned sequence or fragment, the said analogue consisting of a peptide chain in which at least one of the residues is, on the one hand, linked to at least one neighbouring residue via an —NH—CO— linkage, and is, on the other hand, of opposite chirality to that of this same aminoacyl residue in the peptide chain of the parent peptide (that is to say of the above-mentioned sequence or fragment).

The expression "sequence derived by introducing a retro linkage" should be understood as meaning any peptide analogue of the above-mentioned sequence or fragment, the said analogue consisting of a peptide chain in which at least one of the residues is linked to at least one neighbouring residue via an —NH—CO— linkage, the chirality of all of the aminoacyl residues involved in at least one —NH—CO— linkage being conserved relative to the corresponding residues of the peptide chain of the parent peptide.

It goes without saying that the —CO—NH— and —NH—CO— linkages should be considered, in the text hereinabove, in the direction of the parent peptide chain going from the amino-terminal (N-terminal) end to the carboxy-terminal (C-terminal) end.

In the text hereinabove, the expression "protein-generating amino acid" means any amino acid forming part of the constitution of a natural protein or peptide.

In contrast to the preceding definition, the expression "non-protein-generating amino acid" means any amino acid which does not form part of the constitution of a natural protein or peptide. The expression "non-protein-generating amino acid" more particularly means any amino acid whose carbon bearing the side chain R, i.e. the group —CHR—, located between —CO— and —NH— in the natural peptide chain, is replaced with a unit which does not form part of the constitution of a natural protein or peptide.

The invention relates, more particularly, to the derived sequences as described above, characterized in that at least one of the —CO—NH— peptide linkages of the peptide chain of the parent peptide is replaced with a linkage other than the —CO—NH— linkage, the said other linkage being chosen in particular from the following:

—$CH_2$—NH— (methyleneamino);
—$CH_2$—$CH_2$— (carba);
—CO—$CH_2$— (ketomethylene);
—$CH_2$—O— (methylenoxy);
—CHOH—$CH_2$— (hydroxyethylene);

—CHOH—CHOH— (dihydroxyethylene);
—CH=CH— (E or Z olefin);
—CHCN—NH— (cyanomethyleneamino);
—S—CH$_2$— (thiomethylene);
—CH$_2$—S— (methylenethio);
—CS—NH— (thio amide);
—PO$_2$—NH— (phosphonamide);
—CHOH— (hydroxymethylene);
—NH—CO—NH— (urea);

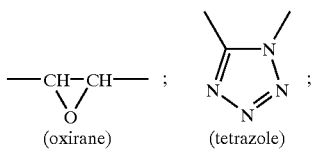

(oxirane)    (tetrazole)

—CH$_2$—CO—NH— (homologation);
—CHOH—CH$_2$—NH— (hydroxyethylene amino);
—CO—NH—NH— (hydrazino).

The peptide sequences corresponding to the IFN-γ C-terminal portion, in the above-mentioned lipopeptides, or the fragments of these sequences, or the sequences derived from these sequences or fragments, as defined above, are advantageously IFN-γ agonists and have at least one biological activity of the mammalian IFN-γ type, that is to say at least one of the following properties:

1) as regards the biological properties:
   an immunoadjuvant effect,
   an antiviral effect,
   an immunomodulatory effect, in particular by:
      stimulating the cellular production of cytokines,
      action on the presentation of antigens, in particular:
         by increasing the expression of class I HLA genes, and of the β2-microglobulin gene; this results in an increase in the possibilities of presentation of antigens foreign to the CD8+ lymphocytes,
         by increasing or inducing the expression of class II HLA genes, and of the invariant chain; this results in an increase in the possibilities of presentation of antigens foreign to the CD4+ lymphocytes,
      action on the cellular adhesion phenomena, by stimulating the synthesis and expression of the VCAM-1 protein at the surface of the various cells (macrophages, endothelial cells), thus promoting the immunological phenomena of cellular cooperation,
   increasing the expression of the complement proteins,
   a maturation effect on the B lymphocytes,
   a maturation effect on the cytotoxic T lymphocytes,
   an activation effect on the NK cells (increase of their cytotoxic activity) pand an inductive effect on the generation of LAK cells (lymphokine-activated killer cells),
   an effect of increasing the cytotoxic possibilities of the monocytic and megakaryocytic lines, in particular by:
      increasing the synthesis of TNFα,
      stimulating the production of oxygenated free radicals,
      producing nitric oxide (NO—),
      inducing the production of tryptophan-derived mediators, such as picolinic acid,
   increasing the release of lysosomal enzymes,
   an action on the inflammatory reaction,
   an effect on fibrinogenesis (anti-fibrinogenic) and on the fibrinolysis and haemostasis system,
   anti-infectious effects;

2) as regards the pharmacological properties:
   an effect of reducing the incidence of infectious complications in patients suffering from chronic granulomatosis,
   effects in infectious immunotherapy, in particular:
      an antibacterial effect,
      an antifungal effect,
      an antiparasitic effect, in particular in the case of leishmaniasis, toxoplasmosis and malaria,
      an anithelmintic effect,
   effects against viral infections,
   effects against atopy and allergic pathologies, in particular pulmonary hypereosinophilic allergies, or skin allergies (dermatitis),
   effects against autoimmune diseases,
   anti-cancer effects, in particular in the case of cancer of the kidneys, cutaneous T lymphomas, chronic myeloid leukaemia, cancer of the ovaries and mesotheliomias.

The present invention also relates to micelles or micro-aggregates of one or more different lipopeptides defined above.

The said micelles or micro-aggregates are advantageously less than about 1 μm in size.

The micelles or micro-aggregates according to the invention are preferably as obtained by dispersing the said lipopeptides in an approximately 80% concentrated acetic acid solution, or any other solvent capable of ensuring molecular dispersion of the lipopeptides in solution.

The invention also relates to any pharmaceutical composition which is characterized in that it comprises one or more lipopeptides, where appropriate in the form of micelles, as described above, and in combination with a vehicle in the context of a physiologically acceptable pharmaceutical formulation.

The invention relates, more particularly, to the use of lipopeptides, where appropriate in the form of micelles, as described above, for the preparation of a medicinal product intended for treating and, where appropriate, preventing pathologies against which IFN-γ is liable to act, in particular against the pathologies listed above in the context of the pharmacological properties of IFN-γ.

The lipopeptides, where appropriate in the form of micelles, mentioned above are advantageously used for the preparation of an antiviral medicinal product intended for treating viral pathologies such as AIDS, conditions caused by papillomaviruses (in particular certain uterine cancers), the various forms of hepatitis, including hepatitis B, or the various non-A non-B hepatitides.

Advantageously also, the above-mentioned lipopeptides, where appropriate in the form of micelles, are used for the preparation of a medicinal product for treating bacterial or viral pulmonary infections, such as tuberculosis or pneumocystosis, or for treating bacterial or viral infections of the ORL area (and more particularly of the bucccopharyngeal area).

The above-mentioned pharmaceutical compositions are preferably in a pharmaceutical form which allows a high concentration of active principle to be obtained in an area of micro-diffusion around the site of parenteral, intramuscular, subcutaneous or intradermal injection, or from a contact surface (intra-pulmonary aerosol or nebulizate, sublingual, transmucous or percutaneous route), or alternatively in a form which can be applied topically, in particular in the form of a cream or ointment.

The preferred dosages of the above-mentioned pharmaceutical compositions for a treatment such as a treatment with IFN-γ should be related to the dosages used in the case of recombinant IFN-γ, given that 2 to 3 μg of lipopeptide according to the invention correspond to 1 IU of IFN-γ. For example, the prescribed doses of recombinant IFN-γ in the context of a clinical trial carried out on patients suffering from metastatic renal carcinoma are 1 mg/m² i.v. per day for 5 days, one week in two, for one month (approximately 4 to 5×10⁶ IU per dose, depending on the specific activity of the batch, set at around 0.2 ng/1 IU (Mani S., Poo W. J., Am. J. Clin. Oncol., 1996, 19: 2, pp. 149–153)).

As immunoadjuvant combined with a vaccine, as described below, the dose of lipopeptide according to the invention is advantageously from about 125 to about 500 μg/ml (on average about 250 μg/ml), for injected volumes of about from 0.5 to 3 ml in man, or in veterinary application.

As an IFN-γ analogue, used alone for its immunostimulatory, anti-cancer or anti-infectious properties, the preferred doses of the lipopeptide of the invention, when it is administered by inhalation or via the intranasal route, of solutions at concentrations of about 25 to 50 μM, are thus from about 250 to 500 μg/ml, i.e. about 1.5 to 3 mg per dose/per day in man (as a general rule, at a rate of 3 times a week, for 6 months).

The invention also relates to any composition characterized in that it comprises one or more lipopeptides, where appropriate in the form of micelles, as described above, in combination with:

one or more peptides or lipopeptides containing one or more epitopes specifically recognized by the cytotoxic T lymphocytes (also referred to as CTLs), and capable of activating the latter (also referred to as CTL epitopes or CD8+epitopes), and/or one or more peptides or lipopeptides containing one or more epitopes specifically recognized by the helper T lymphocytes (also referred to as HTLs), and capable of activating the latter (also referred to as HTL epitopes or CD4⁺ epitopes), and/or one or more peptides or lipopeptides containing one or more B epitopes specifically recognized by antibodies directed against the latter.

The invention relates, more particularly, to any composition as defined above which is characterized in that the said CD8⁺ epitopes are:

those characteristic of tumour cells, such as:
the epitopes of chronic myeloid leukaemia (in particular those listed in Table 1),
the epitopes of protein p53 (in particular those listed in Table 2),
melanoma epitopes (in particular the human melanoma epitopes listed in Table 3), and more particularly the epitopes of the human melanoma melan-A/mart-1 antigen
the epitopes of tumours resulting from mutations (in particular those listed in Table 4),
antigens common to various tumours, such as those listed in Table 5),
those characteristic of viral proteins, such as:
the epitopes of hepatitis B virus (HBV) proteins,
the epitopes of AIDS virus (HIV) proteins (in particular those listed in Table 6),
the epitopes of human papillomavirus (HPV) proteins, in particular the HPV E₆ or E₇ proteins (in particular those listed in Table 7).

The invention relates, more particularly, to any composition as described above which is characterized in that it contains, as CD4⁺ epitopes, multiple epitopes such as the tetanus toxin peptide TT(830–846) (Panina-Bordignon et al., 1989), the influenza haemagglutinin HA(307–319) (Krieger et al., 1991), PADRE (Alexander et al., 1994), the HIV-1 45–69 NEF peptide (Estaquier et al., 1992), the LSA3 peptide of *Plasmodium falciparum*, which is the agent responsible for malaria (Ben Mohamed et al., 1997).

The invention relates, more particularly, to any composition as described above which is characterized in that it contains, as B epitope, one of the epitopes of a protein associated with an allergic reaction, such as the house dust allergens, in particular of the peptides of *Dermatophagoides pteronyssinus* (peptides 52–71, 117–133, 176–187 or 188–199) or of *Dermatophagoides farinae*.

The invention also relates to any lipopeptide as defined above which comprises one or more above-mentioned CD8⁺ and/or CD4⁺ and/or B epitopes, the said epitopes being covalently bonded to the lipophilic portion of the said lipopeptide, and/or to the above-mentioned peptide sequence of the C-terminal end of mammalian IFN-γ, or to fragments or sequences derived therefrom.

The lipopeptides described above are preferably such that their peptide portion comprises one or more above-mentioned CD8⁺ and/or CD4⁺ and/or B epitopes, the said epitopes being covalently bonded (directly or via a sequence of about 2 to 5 amino acids) to the above-mentioned peptide sequence of the C-terminal end of mammalian IFN-γ, or to fragments or sequences derived therefrom. The linkages between the said epitopes and the said peptide sequence of the C-terminal end are preferably peptide linkages, or any of the linkages resulting from simple ligations as mentioned above.

The invention also relates to micelles or micro-aggregates of one or more different lipopeptides which comprise one or more covalently bonded CD8⁺ and/or CD4⁺ and/or B epitopes, as defined above.

As above, the said micelles or micro-aggregates are advantageously less than about 1 μm in size, and are preferably obtained by dispersing the said lipopeptides in an approximately 80% concentrated acetic acid solution.

The invention also relates to any pharmaceutical composition or vaccine which is characterized in that they comprise:

a composition of one or more lipopeptides, where appropriate in the form of micelles, in combination with one or more CD8⁺ and/or CD4⁺ and/or B epitopes, the said composition being as defined above, and/or one or more lipopeptides, where appropriate in the form of micelles, comprising one or more covalently bonded CD8⁺ and/or CD4⁺ and/or B epitopes, as defined above, and optionally one or more lipopeptides as defined above, containing only the above-mentioned peptide sequence of the C-terminal end of IFN-γ, where appropriate in the form of micelles, in combination with a vehicle in the context of a physiologically acceptable pharmaceutical formulation.

The above-mentioned pharmaceutical compositions comprising epitopes are in a pharmaceutical form which allows a high concentration of active principle to be obtained in a microdiffusion area around the site of parental, intramuscular, subcutaneous or intradermal injection, or from a contact surface (intrapulmonary aerosol or nebulizate, sublingual, transmucous or percutaneous route), or alternatively in a form which can be applied topically, in particular in the form of a cream or ointment.

The preferred dosages are as defined above.

A subject of the invention is, more particularly, the use:

of a composition of one or more lipopeptides, where appropriate in the form of micelles, in combination with one or more CD8+ and/or CD4+ and/or B epitopes, the said composition being as defined above, or of one or more lipopeptides, where appropriate in the form of micelles, comprising one or more covalently bonded CD8+ and/or CD4+ and/or B epitopes, as defined above, for the preparation of a medicinal product or vaccine for inducing a specific immune response against the antigens corresponding to the said epitopes, more particularly in the context of treating and, where appropriate, preventing pathologies which can be controlled by activating CTL and/or HTL by means, respectively, of the said CD8+ epitopes linked to the class I CMH molecules, and/or of the CD4+ epitopes linked to the class II CMH molecules, at the surface of antigen-presenting cells, and/or for the preparation of a medicinal product or vaccine for re-orienting the immune response by antibodies directed against B epitopes, and more particularly directed against an allergen.

The invention relates, more particularly, to the above-mentioned use:

of a composition as described above of one or more lipopeptides, where appropriate in the form of micelles, in combination with one or more CD8+ epitopes, or of one or more lipopeptides as defined above, where appropriate in the form of micelles, comprising one or more covalently bonded CD8+ epitopes, in which the epitopes are those characteristic:

of tumour cells, as described above, for the preparation of an anti-tumour medicinal product, intended for the treatment of tumour pathologies such as chronic myeloid leukaemia, or melanoma, or of viral proteins, as described above, for the preparation of a medicinal product or vaccine intended for preventing and, where appropriate, treating viral pathologies such as AIDS, conditions caused by papillomaviruses (in particular certain uterine cancers), the various forms of hepatitis, including hepatitis B, or the various non-A non-B hepatitides.

The invention relates, more particularly, to the above-mentioned use:

of a composition as described above of one or more lipopeptides, where appropriate in the form of micelles, in combination with one or more CD4+ epitopes, or of one or more lipopeptides as defined above, where appropriate in the form of micelles, comprising one or more covalently bonded CD4+ epitopes, in which the said CD4+ epitopes are multi-specific epitopes capable of potentiating the immune response against any other antigen in an unselected population, and are in particular those characteristic of tetanus toxin TT(830–846), the influenza haemagglutinin HA(307–319), PADRE, the HIV-1 45–69 NEF peptide, and the LSA3 peptide of *Plasmodium falciparum*, mentioned above, for the preparation of a medicinal product or vaccine for potentiating the immune response against any other antigen, in particular in the context of viral or parasitic pathologies.

The invention relates, more particularly, to the above-mentioned use:

of a composition as described above of one or more lipopeptides, where appropriate in the form of micelles, in combination with one or more B epitopes, or of one or more lipopeptides as defined above, where appropriate in the form of micelles, comprising one or more covalently bonded B epitopes, in which the epitopes are those characteristic of proteins associated with an allergic reaction, such as the B epitopes corresponding to the allergens of house dust, in particular the peptides of *Dermatophagoides pteronyssinus* (peptides 52–71, 117–133, 176–187 or 188–199), or of *Dermatophagoides farinae*, for the preparation of a medicinal product or vaccine intended for preventing and, where appropriate, treating allergic pathologies such as allergic asthma.

The invention also relates to the use of any lipopeptide or of any lipopeptide composition, as described above, in the context of carrying out methods for the in vitro (or ex vivo) treatment of cells of the human or animal body, the said method comprising a step of taking the said cells from the human or animal, who or which is healthy or requires a treatment, followed by a step of treating the said cells by incubating them with a lipopeptide or a lipopeptide composition according to the invention, and a step of administering the cells thus treated to the patient from whom they were taken, or to any other patient requiring such a treatment.

The invention also relates to the use of lipopeptides as defined above, where appropriate in the form of micelles, as laboratory reagents, in particular:

to reproduce the cellular activation effects of IFN-γ, by adding the lipopeptides according to the invention to cells in order to activate them before carrying out other explorations on these cells, as immunoadjuvant to test the immune response of a vaccinating principle under study, as immunomodulator, that is to say for its ability to polarize the immune response.

The invention also relates to any peptide whose sequence is delimited on the N-terminal side by an amino acid located in one of the positions 113 to 121, and on the C-terminal side by the amino acid located in position 132, of the murine IFN-γ peptide sequence represented above.

In this respect, the invention relates, more particularly, to the peptide delimited by the amino acids located in positions 113 and 132 of the murine IFN-γ peptide sequence, and corresponding to the sequence below:

SEQ ID NO: 1

The invention also relates to any peptide as described above which is characterized in that the COOH function of the C-terminal amino acid is substituted with a group which is resistant to the organism's exopeptidases, in particular with a carboxamide group.

The above-mentioned peptide sequences used in the context of the present invention are advantageously synthesized chemically, in particular according to the conventional techniques of solid phase peptide synthesis described in the experimental section which follows.

As a variant, the above-mentioned peptide sequences can be obtained via genetic engineering, in particular by transforming suitable host cells with vectors containing the DNA sequences encoding the said peptide sequences.

The invention will be further illustrated with the aid of the detailed description which follows, of the preparation of lipopeptides according to the invention, as well as of the studies of their biological properties.

A) Study of the MuL Peptide

I—Peptide Synthesis of the MuL Lipopeptide According to the Invention

The following peptide, also referred to as the Mu peptide, and corresponding to the sequence delimited by the amino acids located in positions 95 and 132 of the murine IFN-γpeptide sequence, was synthesized.

SEQ ID NO 22

The following modifications were carried out on the Mu peptide:

- a carboxamide end was introduced at the C-terminus to reinforce the stability with respect to exopeptidases,
- the N-terminal end of the peptide was modified with an N$^\alpha$-acetyl-Lysine N$^\epsilon$(palmitoyl) group, to allow penetration of the peptide across the membrane independently of the cellular activity.

The Mu peptide thus modified was denoted as MuL, and is represented by the following formula:

(Ac—K(Pam)=N$^\alpha$-acetyl-Lysine N$^\epsilon$(palmitoyl))     SEQ ID NO 20

A control lipopeptide, also referred to as "scrambled", corresponding to the MuL lipopeptide in which the order of the amino acids has been arranged so as to avoid any sequential relationship with the peptide of origin, was synthesized. This control lipopeptide is obtained from the MuS peptide of the following formula:

SEQ ID NO 23 and was denoted as peptide MuSL Ac—K(Pam); it corresponds to the following formula:

SEQ ID NO 24

Non-lipid analogues of the above-mentioned peptides were also synthesized, with the aim of carrying out comparative studies:

Mu peptide: SEQ ID NO 22

MuS peptide: SEQ ID NO 23

Peptide synthesis: The peptides were synthesized on an MBHA resin (0.63 mmol/g, Applied Biosystems, Foster City, USA) using the Boc-benzyl strategy (Merrifield, R. B., 1963; Merrifield, R. B., 1986) and the in situ neutralization protocol, using an AB1 430A peptide synthesizer (Foster City, USA). The protected amino acids are obtained from Propeptide (Vert-le-Petit, France). The side chains are protected as follows: Arg(Tos), Thr(Bzl), Asp(OcHex), Glu(OcHex), Gln(Trt), Asn(Trt), Lys(2-ClZ), His(Bom). An acetylation was carried out systematically after each recoupling on the N-terminal function, using 10% acetic anhydride and 5% DIEA in $CH_2Cl_2$.

In order to obtain the lipopeptide, an N-terminal lysine was introduced via Boc-L-Lys(Fmoc)-OH (France Biochem, Meudon, France). At the end of the synthesis, the Fmoc group was removed with 20% piperidine in DMF. The lipopeptide is obtained after selective acylation of the ε-amino group of the N-terminal Lys on the peptidyl-resin (palmitic acid/HBTU/DIEA : 4 eq/4 eq/12 eq in DMF for 30 min, ×2). The lipopeptide is cleaved from the resin (dry resin/HF/p-cresol/thiocresol: 1 g/10 ml/0.75 g/0.25 g, 1 h 30 min at 0° C.) and lyophilized. The purification is carried out by several RP-HPLC chromatographies on a C18 Nucleosil column (12.5 mm×500 mm, solvent A: $H_2O$ containing 0.05% TFA; solvent B: $MeCN/H_2O$: 4/containing 0.05% TFA). The homogeneity is confirmed by RP-HPLC on C3 Zorbax (4.6×250 mm). Using 0.25 mmol of MBHA resin, 140 mg (cumulative yield of 10%) of lipopeptide with a purity of greater than 95% are obtained. The identity was confirmed by determining the amino acid composition after total acid hydrolysis, and by determining the molecular mass by TOF-PDMS (Bio-Ion 20 Plasma Desorption Mass Spectrometer): [MH$^+$] calc.: 4980.9; obs.: 4982.7.

II—Summary of the Biological Results

All the tests mentioned below have in common the use of complete culture media, without removing the foetal calf serum, or introducing any protease inhibitor in order to be under the optimum cell culture conditions without, however, attempting to protect the peptide constructs from possible degradations due to components intrinsic to the culture medium used.

1—Induction of Class II CMH Molecules:

Principle: to check the induction of class II CMH molecules on cell lines (P388D1 and WEHI3: murine myelomonocytes) with the above-mentioned peptides.

Procedure. The cells are cultured the day before at a rate of 3×10$^5$ cells per well in 24-well culture plates (NUNC). The following day, the cells are stimulated with the various lipopeptide and peptide constructs at a final concentration of 50 μM in 1 ml of medium. After incubation for 24 hours at 37° C. in an atmosphere saturated with 5% $CO_2$, the cells are recovered and incubated for 1 hour at 4° C. with 3 μg of a biotinylated mouse anti-I-Ad monoclonal antibody (Pharmingen, San Diego, USA). After revelation for 30 minutes with FITC streptavidin used at a dilution of 1:100 (Sigma, St. Louis, USA), the expression of class II molecules is determined by flow cytometry.

Results. Table 8 below represents the percentage of class II CMH detected by flow cytometry, on the various cell lines stimulated for 24 hours with the various peptide constructs.

TABLE 8

| name of the peptide | P388D1 | WEH1 |
|---|---|---|
| untreated cells | 3 | 3 |
| Mu | 5 | 8 |
| MuS | 14 | 5 |
| MuL | 98 | 64 |
| MuSL | 13 | 15 |

As observed by Szente (Szente et al., 1994), the induction of the class II CMH molecules is at a maximum after stimulation for 24 hours, whereas with recombinant IFN-γ, it reaches its maximum after 48 hours; this suggests that the synthetic constructs would effectively allow a faster activation of the signal transduction pathway.

Furthermore, the lipopeptide construct is more active than the non-vectorized peptide at the concentration studied. This is due to the presence of the grafted palmitic acid, which gives the lipopeptide better cytoplasmic addressing. In the light of these results, the study was extended on cells taken from an animal (Balb/c mouse) in order to be able to evaluate the potential of MuL in ex vivo studies.

2—Induction of the Expression of Class II CMH Molecules and of Fc-γ Receptors (Fc-γ R) on Splenocytes and Peritoneal Cells Taken From an Animal (Balb/c mouse).

Principle: to evaluate the activity of the vectorized agonist on cells taken from an animal and treated in vitro (in order to assess the value of a subsequent in vivo study).

Procedure. The splenocytes and peritoneal cells taken from an animal (Balb/c mouse) are re-cultured at a rate of 2.5×10$^6$ splenocytes and 106 peritoneal cells per well in 24-well plates (NUNC) stimulated with 50 μM of the different peptides in a final volume of 1 ml. After stimulation for 24 hours, the cells are labelled with the anti IA$^d$ monoclonal antibody described in the preceding paragraph, according to the same protocol. To detect the Fc-γ R, the cells are labelled with 1 μg of a rat anti Fc-γ R monoclonal antibody (Pharmingen, San Diego, USA). Next, the cells are incubated for ½ hour with a rat anti IgG biotinylated polyclonal antibody. The revelation is then carried out with FITC streptavidin used at a dilution of 1:100 (Sigma, St. Louis, USA). The expression of Fc-γ R is determined by flow cytometry.

Results. The percentage of $IA^d$ and Fc-γ R detected by flow cytometry on splenocytes and peritoneal cells taken from the animal is represented in Table 9 below.

TABLE 9

| name of the peptide | splenocytes | | peritoneal cells | |
| --- | --- | --- | --- | --- |
| | RFc (%) | II CMH (%) | RFc (%) | II CMH (%) |
| untreated cells | 9 | 10 | 6 | 5 |
| Mu | 7 | 12 | 8 | 13 |
| MuS | 8 | 9 | 8 | 6 |
| MuL | 75 | 83 | 45 | 60 |
| MuSL | 15 | 14 | 20 | 13 |

A marked increase of $IA^d$ and of Fc-γ R may be observed on the cells treated with MuL, whereas its scrambled lipopeptide control has no notable activity. Furthermore, the activity of MuL is markedly higher than that of Mu; this again confirms the undeniable advantage afforded by adding palmitic acid. These results show that the activity observed is not limited to one or two types of cell lines, but that it is also observed on cells taken from an animal, and this being independent of their cellular function.

3—Confirmation of the Involvement of the IFN-γ Receptor

Principle. to confirm that the biological activity observed was effectively associated with a stimulation of the IFN-γ receptor, we repeated the same experiments, in parallel on splenocytes taken from mice 129 (Wild type: WT) and on cells taken from mice 129 no longer expressing the alpha chain of the IFN-γ receptor (KO mice).

Procedure. The experimental protocol followed is identical to that described in paragraph 2 above.

Results. Table 10 below shows the results obtained following stimulation for 24 hours of cells taken from KO animals for the a chain of the IFN-γ receptor. The expression of $IA^d$ and of Fc-γ R is analysed by flow cytometry.

TABLE 10

| name of the peptide | WT mice | | KO mice | |
| --- | --- | --- | --- | --- |
| | RFc (%) | II CMH (%) | RFc (%) | II CMR (%) |
| untreated cells | 1 | 4 | 1 | 3 |
| Mu | 1 | 12 | 1 | 3 |
| MuS | 1 | 3 | 1 | 3 |
| MuL | 23 | 52 | 3 | 4 |
| MuSL | 2 | 4 | 3 | 4 |

It can be seen that MuL is capable of inducing the expression of $IA^d$ and of Fc-γ R on the cells taken from the wild type animal, whereas no similar activity is obtained on the cells taken from the animals which are deficient in respect of the IFN-γ receptor. This provides proof that the activity of MuL acts via an interaction with the cytokine receptor, and thereby confirms the specificity of the biological activity observed with an agonist. Consequently, the vectorized construct (or lipopeptide) induces the expression of II CMH and of Fc-γ R via an interaction with the receptor for this cytokine.

4—Confirmation of the Intracellular Penetration of the Vectorized Agonist, Onfirmation of the Potential of MuL to Stimulate Human Cells.

Principle: murine IFN-γ is incapable of stimulating human cells, unless acting intracellularly: the demonstration of a biological activity induced by the MuL lipopeptide on human cells consequently means that the peptide has been able to interact with the internal portion of the IFN-γ receptor, and constitutes indirect proof of the penetration of the lipopeptide into the cytoplasmic compartment.

Procedure. A primary culture of human dermal cells at confluence in a 96-well plate (NUNC) is stimulated with the various peptide constructs at a final concentration of 25 and 50 μM (in a final volume of 100 μl) or with human IFN-γ for 24 hours. Next, the expression of VCAM-1 adhesion molecules is evaluated by "cell-ELISA". To do this, the cells are labelled at 4° C. with 0.5 μg of a mouse anti VCAM-1 monoclonal antibody (Pharmingen, Cambridge, USA). The cells are then fixed with paraformaldehyde and labelled using a peroxidase-coupled goat anti-mouse Ig(G, A and M) polyclonal antibody. A revelation with o-phenylenediamine (OPD) is carried out and the plates are read with a spectrometer at 492 nm.

Results. The histogram in FIG. 1 shows the expression of VCAM-1 on the human dermal cells stimulated for 24 hours with the various constructs. The results are expressed as an expression index, giving the activity of human IFN-γ (500 U/mL: 75 ng/mL) a value of 1.

A marked induction of VCAM-1 is noted on the cells treated with the vectorized agonist (i.e. the MuL lipopeptide). This induction is dose-dependent: specifically, a differential expression of VCAM-1 is observed depending on whether the cells were treated with 25 or 50 μM of peptide. The effect of the control construct (MuSL) can be explained by the production of certain inflammatory cytokines such as TNF by these cells in response to a state of stress due to the presence of the lipopeptide at high concentration. However, a marked difference in stimulation is observed between MuL and MuSL. These results establish the cytoplasmic addressing of the vectorized agonist, which conserves its biological activity, as confirmed by the observed induction of VCAM-1. Furthermore, they establish that MuL is capable of stimulating cells in a heterologous system, confirming a certain level of potential of the vectorized agonist for use in a human system.

5-Induction of the Class II CMH Molecule (HLA-DR) on a Human Cell Line.

Principle: human colon carcinoma cells (COLO 205) are analysed for their ability to express HLA-DR after having been stimulated with the various peptide constructs.

Procedure. The cell line COLO 205 is cultured at a rate of $3\times10^5$ cells per well in a 24-well culture plate (NUNC). The following day, the cells are stimulated with the various peptide constructs at a final concentration of 50 μM in 1 ml of medium, and are incubated at 37° C. for 24 hours. The cells are then recovered and labelled using 3 μg of an anti HLA-DR mouse biotinylated monoclonal antibody (clone L243). After revelation with FITC streptavidin, the cells are analysed by flow cytometry.

Results.

Table 11 below shows the percentage of expression of HLA-DR quantified by flow cytometry on COLO 205 cells treated or not treated with 50 μM of MuL or of MuSL.

TABLE 11

| | Untreated cells | MuL | MuSL | Mu |
| --- | --- | --- | --- | --- |
| % HLA-DR | 0.9 | 46.1 | 8.9 | 1.2 |

A marked induction of the expression of HLA-DR is observed on the COLO 205 cells stimulated with MuL; this result confirms on a second model the immunostimulatory potential of MuL in a heterologous system. The control scrambled lipopeptide and the reference peptide described by Szente 5mu) [sic] have no activity in this model.

6 Induction of HLA-DR, ICAM-1 and VCAM-1 on Human Peripheral Blood Mononuclear Cells (PBMC).

Principle. In the light of the results obtained on the human cell line and on human primary cultures, the immunostimulatory potential of MuL was evaluated on human cells taken directly from a healthy donor.

Procedure. PBMCs are isolated from a bag of blood and the cells are then cultured and stimulated for 24 hours with 25 and 50 μM of MuSL or MuL in a final volume of 1 ml. The cells are then recovered and labelled for the expression of VCAM-1, ICAM-1 and HLA-DR according to the protocol already described above. Finally, the cells are analysed by flow cytometry.

Results: table 12 below shows the percentage of VCAM-1, ICAM-1 and HLA-DR detected on PBMCs stimulated for 24 hours with MuSL and MuL.

TABLE 12

|  | Untreated cells | MuL 25 μM | MuL 50 μM | MuSL 25 μM | MuSL 50 μM |
|---|---|---|---|---|---|
| HLA-DR | 24.2 |  | 98.9 |  | 58.3 |
| VCAM-1 | 17.9 | 62.6 | 97.1 | 39.7 | 86.9 |
| ICAM-1 | 16.9 | 44 | 67.9 | 29.4 | 32 |

The results obtained on the PBMCs establish that MuL can induce, in a dose-dependent manner, the expression of VCAM-1, ICAM-1 and HLA-DR on cells freshly taken from a patient. Despite an effect observed with MuSL, which might be due to the lipopeptide itself, a marked induction of the various surface labels studied is observed on the cells treated with MuL. These results indicate that it is possible to use MuL in man.

7. Antiviral Effect

Principle: after having established in a human and a murine system that MuL was capable of stimulating various cell types and of inducing the expression of various surface labels, the ability of MuL to activate a cell function, reflected by an effector function, was evaluated. To do this, we studied the induction of an antiviral state on cells infected with the VSV virus. The induction of the antiviral state corresponds to the total use of all the transduction pathways activated by the natural cytokine. This test constitutes the standard test for assaying the activity of recombinant IFN-γ batches.

Procedure.

L929 cells (mouse fibroblasts) are stimulated for 6 hours with murine IFN-γ, MuSL or MuL at different concentrations. After incubation for 24 hours, VSV is added and the cells are incubated at 37° C. for 24 hours. The cells lysed with the virus are then removed by washing and the live cells are stained using a vital stain, a 1% solution of crystal violet. The staining with crystal violet is finally quantified by reading on a spectrophotometer at 570 nm.

Figure 2:
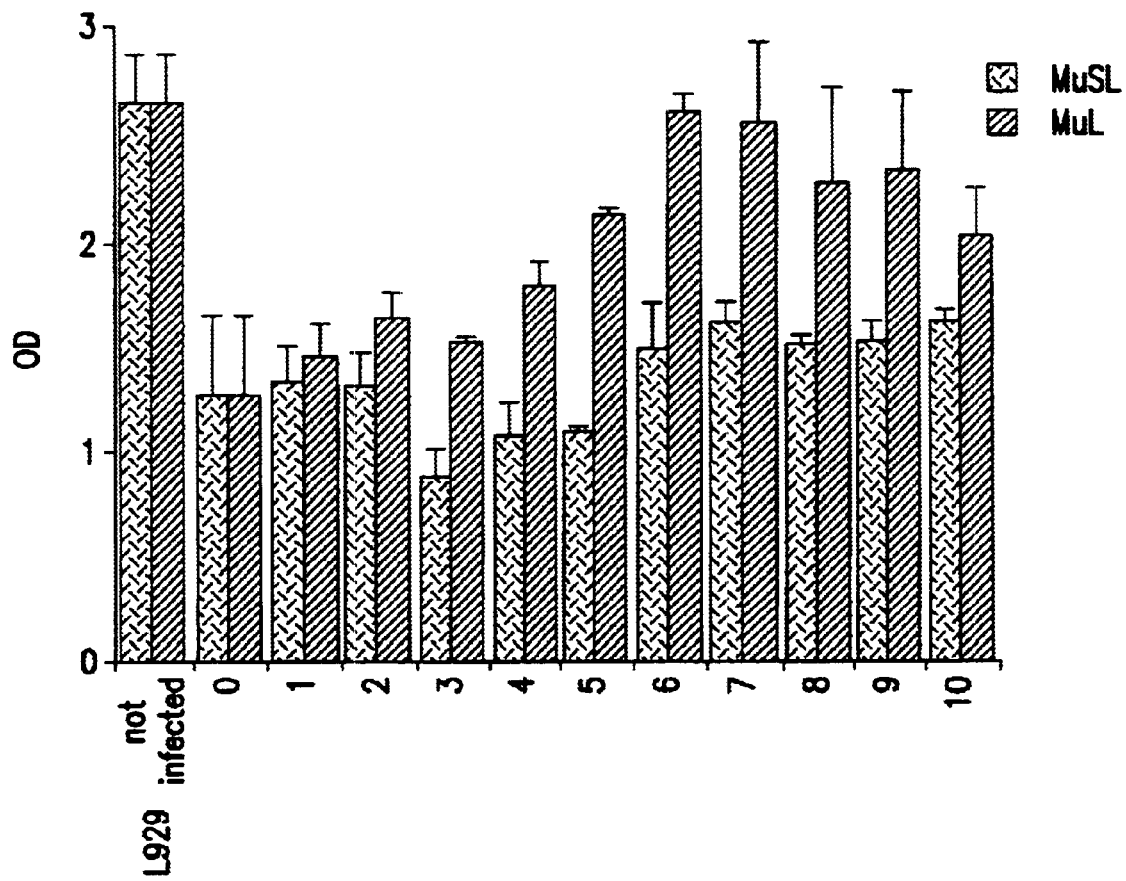
Figure 3:
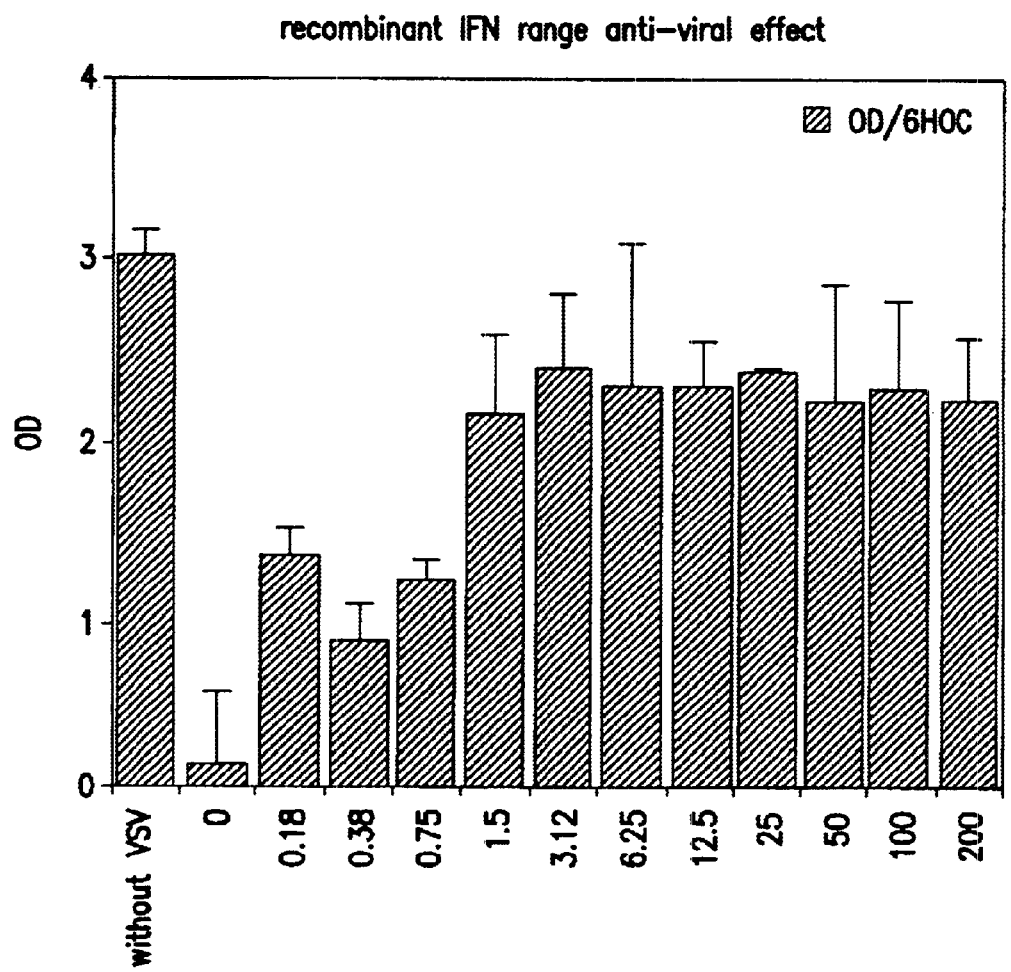

Results. The histogram represented in FIG. 2 shows the results of the antiviral test carried out on L929 fibroblasts treated with the MuSL or MuL peptides. The live cells are stained with crystal violet and this staining is quantified by reading on a spectrophotometer at 570 nm. The black bars represent MuL and the white bars represent MuSL. The histogram represented in FIG. 3 shows the results of the antiviral test carried out on L929 fibroblasts treated with recombinant IFN-γ.

The results obtained show a resistance to viral lysis in the cells treated with MuL, whereas the MuSL control construct has no effect on viral lysis. This is noteworthy at very low concentrations of peptides and thus establishes that MuL is capable of inducing an antiviral state on cells. Furthermore, this test makes it possible to assay the biological activity of our product with reference to the natural cytokine. This test makes it possible to establish that 1 IU of IFN-γ is contained in 5 to 6 μM of peptide, i.e. 2 to 3 μg of product. Given that this activation of an antiviral state is characteristic of IFN-γ, it may thus be concluded therefrom that MuL is capable of reproducing the effects of the cytokine.

III. Conclusion

These studies establish that the peptide derived from the C-terminal domain of IFN-γ modified with a palmitic acid is capable in all respects of mimicking the effect of the cytokine, irrespective of the type of cell used. It was thus established that its action takes place via an interaction with the cytokine receptor. Furthermore, the results obtained in a heterologous system (human cells) and more particularly on cells freshly taken from patients confirm the fundamental value of the MuL construct. Specifically, this construct, which is found to be a powerful immunostimulator, which potentiates the antigenic presentation, which activates cell effector functions both on mouse cells and on human cells, can have a certain degree of therapeutic value, both via an immunostimulatory action and via an immunoadjuvant effect.

B) Immunomodulatory Potential of the MuL Lipopeptide Agonist of IFN-γ

I. Effect on the Activity of IL-4

It is commonly described that the immunomodulatory potential of IFN-γ lies in its ability to polarize the establishment of a type-1 T helper (Th1) response, while at the same time inhibiting the development of a type-2 T helper (Th2) response. This inhibitory action on the polarization of the Th2 response takes place mainly via inhibition of the activity of IL-4. Thus, in order to show that the IFN-γ synthetic agonist is capable of inhibiting the biological effect of IL-4 on splenocytes taken from mice, we used the following cell system. The stimulation of splenocytes with an anti-CD40 antibody (antibody directed against a surface cell label: CD40) and IL-4 induces a proliferation of the murine B cells, following a synergistic action between the CD40 and IL-4 stimulation (Hasbold et al. 1994).

1. Procedure

The splenocytes taken from Balb/c mice are cultured and stimulated with anti-CD40 (10 μg/ml) and IL-4 (10 U/ml). 10 μM of the synthetic agonist of IFN-γ (MuL) or of its control lipopeptide (MuSL) are added. After stimulation for 24 hours, tritiated thymidine is added at a rate of 0.5 μCurie per well. After incubation for 18 hours, the cells are filtered off and the incorporation of tritiated thymidine is evaluated. This incorporation is proportional to the cell proliferation.

2. Results

Figure 4:
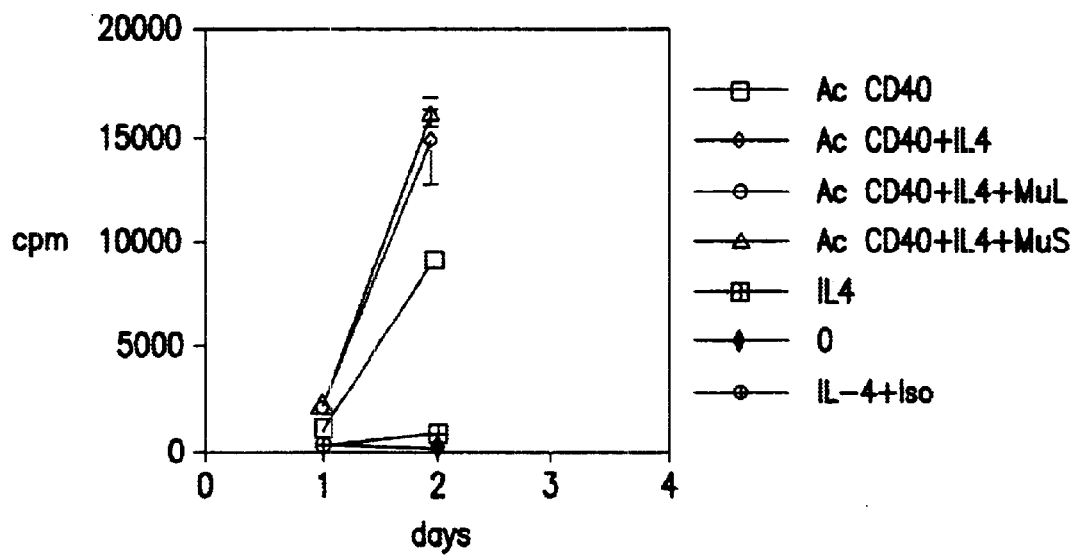

The stimulation of the murine splenocytes with anti-CD40 (Ac CD40) results in a proliferation of the cells (FIG. 4). When IL-4 is added, there is a synergistic action of this cytokine and of the anti-CD40 on the cell proliferation. This proliferation is specific to the anti-CD40 and the IL-4, since IL-4 plus a control isotype antibody (Iso), have no effect on the cell proliferation.

The addition of 10 μM of MuL results in an inhibition of the synergistic effect of the anti-CD40 and the IL-4 on the proliferation of murine splenocytes. The level of proliferation in the presence of MuL is identical to that of the cells stimulated with the anti-CD40 alone. The CD40+IL-4 synergistic effect is thus completely abolished. This is specific to the IFN-γ agonist, since the addition of the control lipopeptide (MuSL) has no effect on the CD40/IL-4-dependent proliferation.

Thus, this experiment establishes that the synthetic agonist of IFN-γ inhibits the biological activity of murine IL-4.

In order to demonstrate that the inhibition of the activity of IL-4 with MuL is specific to an IFN-γ agonist activity, it is thus established that this inhibitory activity of MuL is restricted to cells which express a functional IFN-γ receptor.

Thus, similar experiments were reproduced on cells taken from mice which are deficient for the α chain of the IFN-γ receptor (IFN-γR KO) and on mice of the same genetic background and expressing a functional IFN-γ receptor (WT mice).

Figure 5:
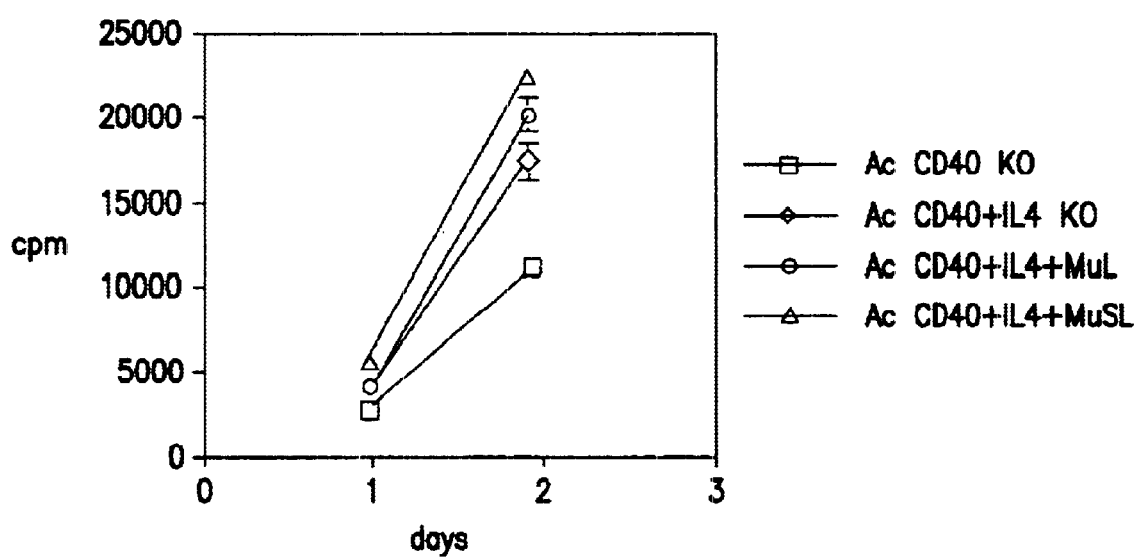
Figure 6:
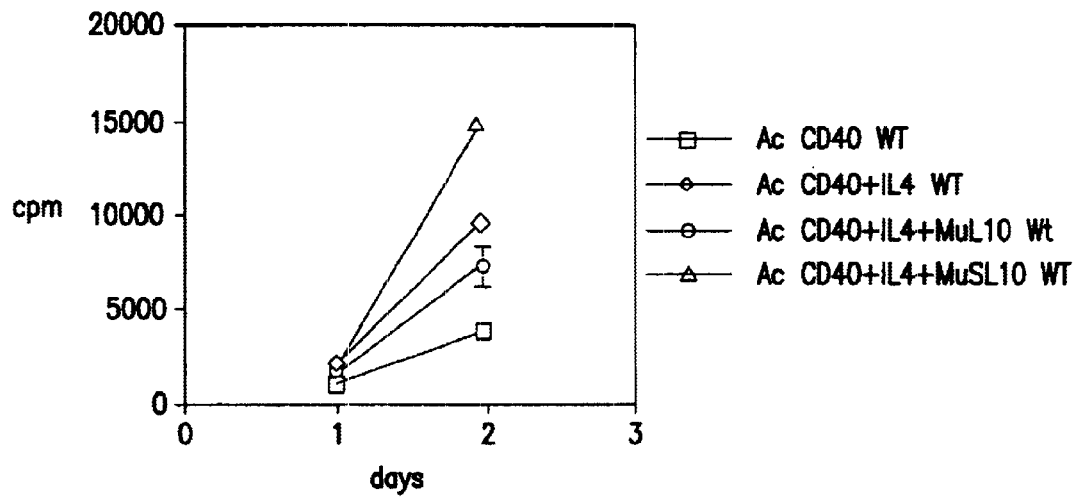

The results in FIGS. 5 and 6 demonstrate that the inhibition of the biological activity of IL-4 with MuL is specific to an "IFN-γ like" activity, and that this activity takes place via the cytokine receptor.

The ability of the synthetic agonist to modulate the biological effects of IL-4 suggests that MuL can be used in vivo, in particular in models of pulmonary hypersensitivity, given the prevalence of type-2 cytokines in such pathologies. Specifically, by way of example, it has been shown in mice that the intranasal administration of recombinant IFN-γ inhibits the development of a pulmonary allergic response (Lack et al., 1996). Furthermore, the ability of the IFN-γ agonist to inhibit the activity of IL-4 should facilitate, in vivo, the establishment of an immune response of Th1 type, which suggests that this synthetic construct can be used in vivo, as an immunomodulator, allowing preferential polarization of a Th1 immune response.

II. Effect on the Synthesis of Immunoglobulins

In order to study in vitro the effect of MuL on the synthesis of immunoglobulins and to be able to assess the effects of the agonist on the establishment of a humoral response in vivo, murine splenocytes with anti-CD40 were stimulated in vitro in the presence or absence of MuL.

1. Procedure

The splenocytes are stimulated under the following conditions:
- unstimulated cells (0)
- cells stimulated with 10 μg/ml of anti-CD40 (aCD40)
- cells stimulated with 10 μg/ml of anti-CD40+MuL 10 μM (aCD40+MuL)
- cells stimulated with 10 μg/ml of anti-CD40+MuSL 10 μM (aCD40+MuSL)
- cells stimulated with the isotypic control of anti-CD40 (Iso)
- cells stimulated with the isotypic control of anti-CD40+MuL 10 μM (Iso+MuL)
- cells stimulated with the isotypic control of anti-CD40+MuSL 10 μM (Iso+MuSL).

2. Results

Figure 7:
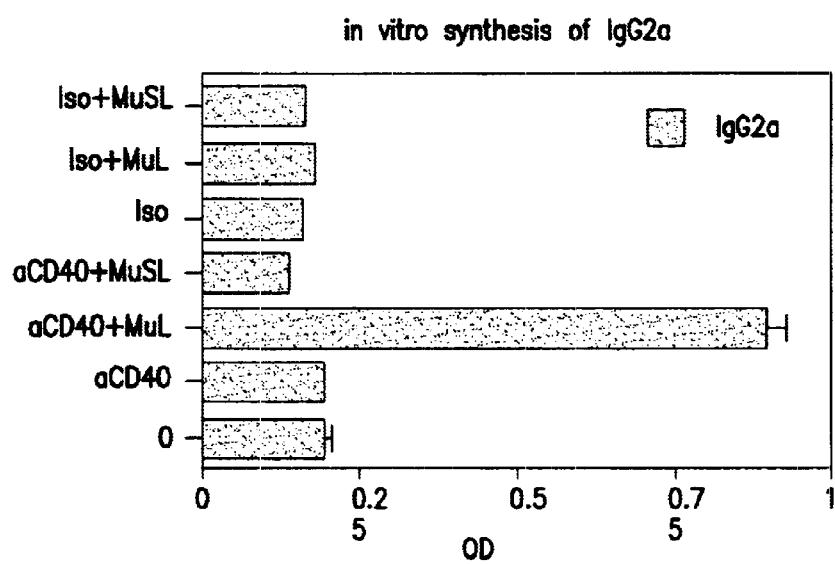
Figure 8:
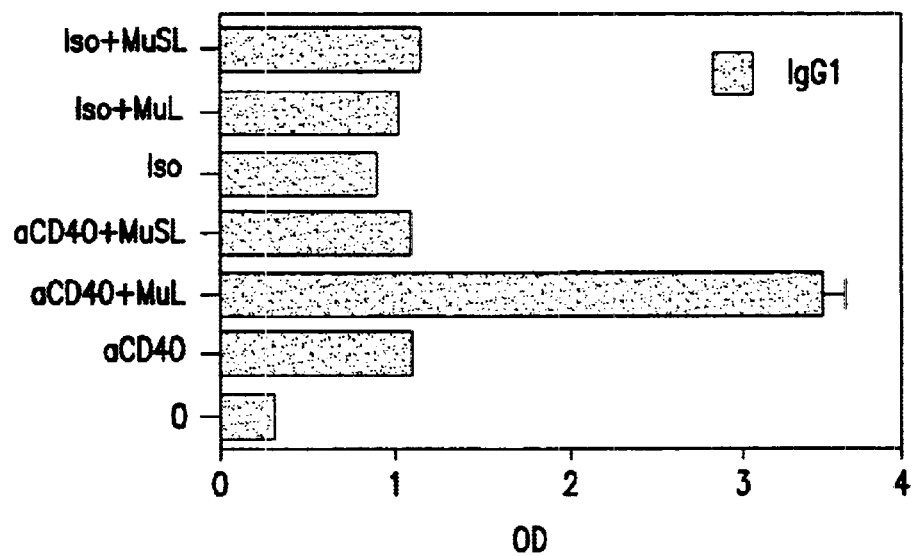
Figure 9:
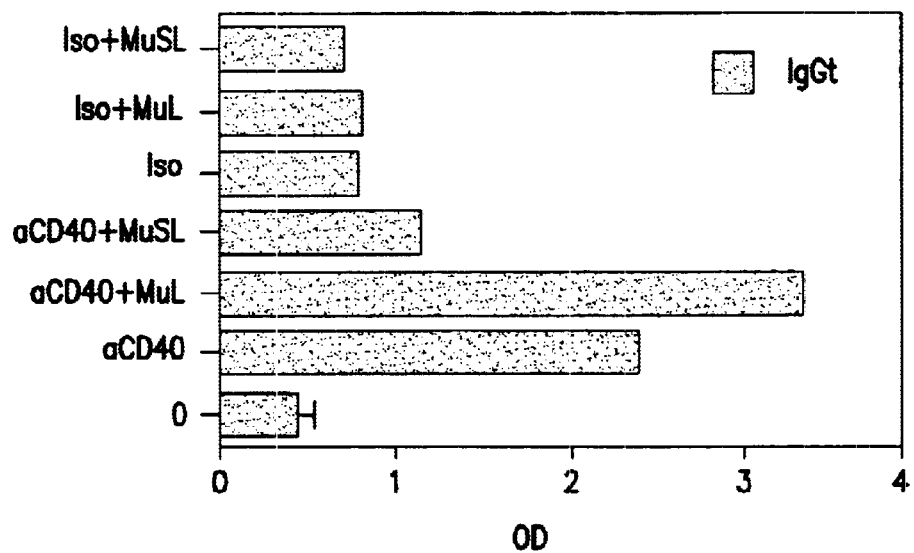

The results shown in FIGS. 7, 8 and 9 show that MuL potentiates the production of total IgG2a, IgG1 and IgG by splenocytes stimulated with an anti-CD40. This effect of MuL on the production of immunoglobulins may be the consequence of a helper effect of the agonist which is thought to stimulate the production of cytokines which would themselves promote the synthesis of immunoglobulins.

These results show that MuL can in vivo, inter alia, contribute towards the establishment of the humoral response, and potentiate the immunity following the injection of certain antigens which induce a humoral response.

III. Ex Vivo and In Vivo Study

In order to study the capacity of the MuL synthetic agonist of IFN-γ to stimulate the production of antibodies in vivo, the following protocol was selected.

1. Procedure

Mice which are transgenic for the T cell receptor, specifically recognizing the Ova peptide (323–339) (Murphy et al., 1990) derived from chicken ovalbumin, are immunized under the following conditions:
- 1—subcutaneous injection of 50 μg of Ova peptide (Ova)
- 2—subcutaneous injection of 50 μg of Ova peptide+50 μg of MuL (MuL+Ova)
- 3—subcutaneous injection of 50 μg of Ova peptide+50 μg of MuSL (MuSL+Ova)
- 4—subcutaneous injection, 24 hours before the immunization, of 50 μg of MuL, followed by immunization the next day with 50 μg of Ova peptide (MuL 24 H and then Ova)
- 5—subcutaneous injection, 24 hours before the immunization, of 50 μg of MuSL, followed by immunization the next day with 50 μg of Ova peptide (MuSL 24 H and then Ova)

The animals are sacrificed 15 days after the immunization. Their splenocytes are cultured and re-stimulated in vitro with 10 μg/ml of anti-CD40 (1, 2, 3, 4, 5 and then aCD40) in the presence or absence of MuL (1, 2, 3, 4, 5 and then aCD40+MuL) or of MuSL (1, 2, 3, 4, 5 and then aCD40+MuSL) in order to be able to study the synthesis of immunoglobulins. The immunoglobulin isotypes are determined by a conventional ELISA technique.

2. Results

The comparative study of the immunization with Ova and MuL and Ova+MuSL shows a potentiation of the production of IgG2a following an aCD40+MuL re-stimulation, of cells taken from animals immunized with Ova+MuL. These results suggest that under conditions of secondary immunization, there is an increase in the production of IgG2a in these animals. Given that this antibody isotype is associated with a type-1 response in the mouse, it may be assumed that MuL has allowed a preferential polarization of the immune response towards a Th1 response. It is also important to note that the injection of MuL 24 hours before immunization with Ova potentiates the synthesis of Ig2A. It thus appears that the synthetic agonist has allowed a preferential initiation of the immune response, which may explain the synthesis of IgG2a and the Th1 polarization.

In contrast with the previous results (FIG. 10), the immunization with MuL+Ova does not potentiate the synthesis of IgG1. This confirms the polarisation of the immune response observed in the experiment described in FIG. 10. Specifically, it is commonly described that IFN-γ acts on the humoral response by promoting the synthesis of IgG2a to the detriment of that of IgG1.

Figure 10:
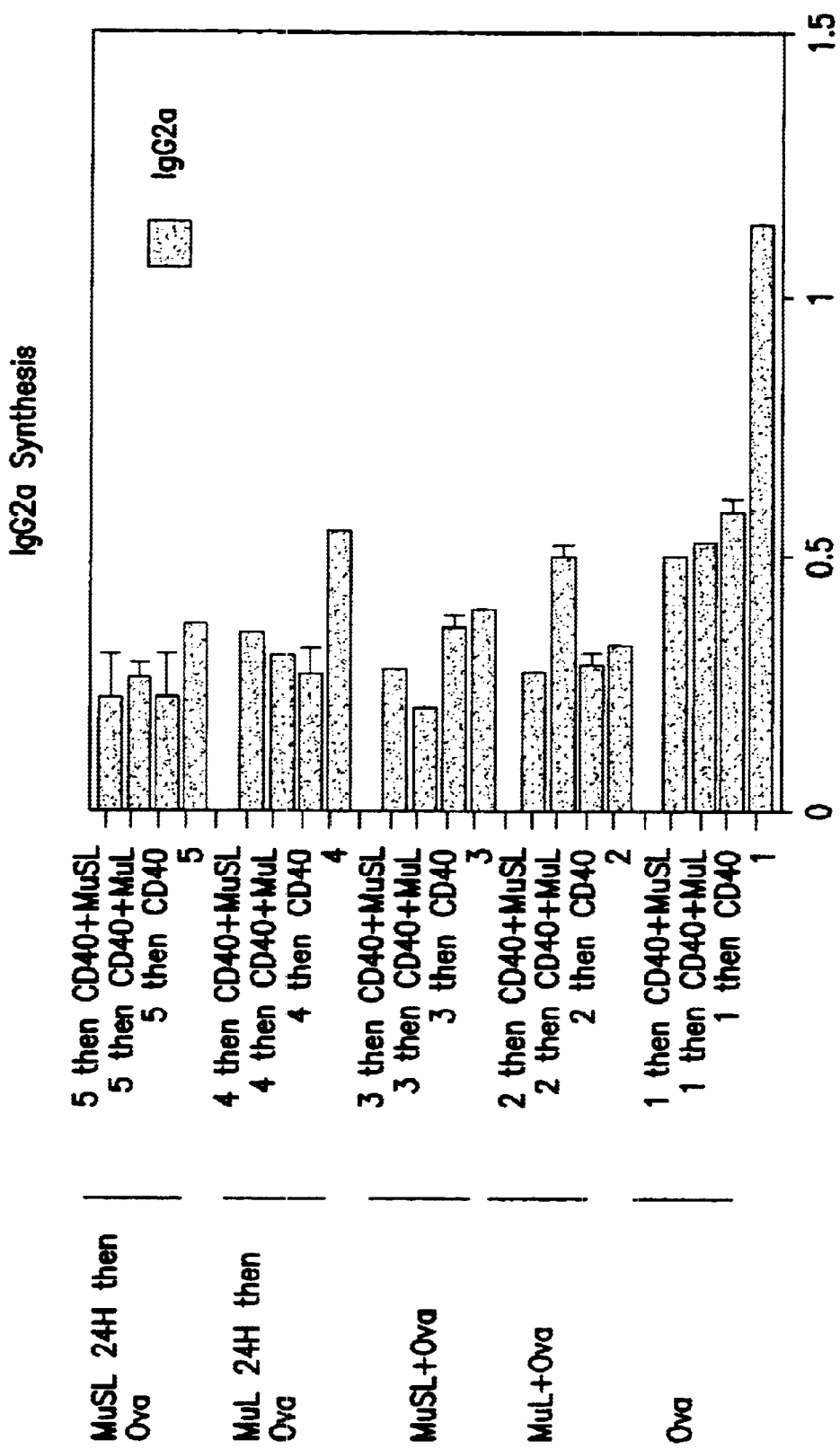
Figure 11:
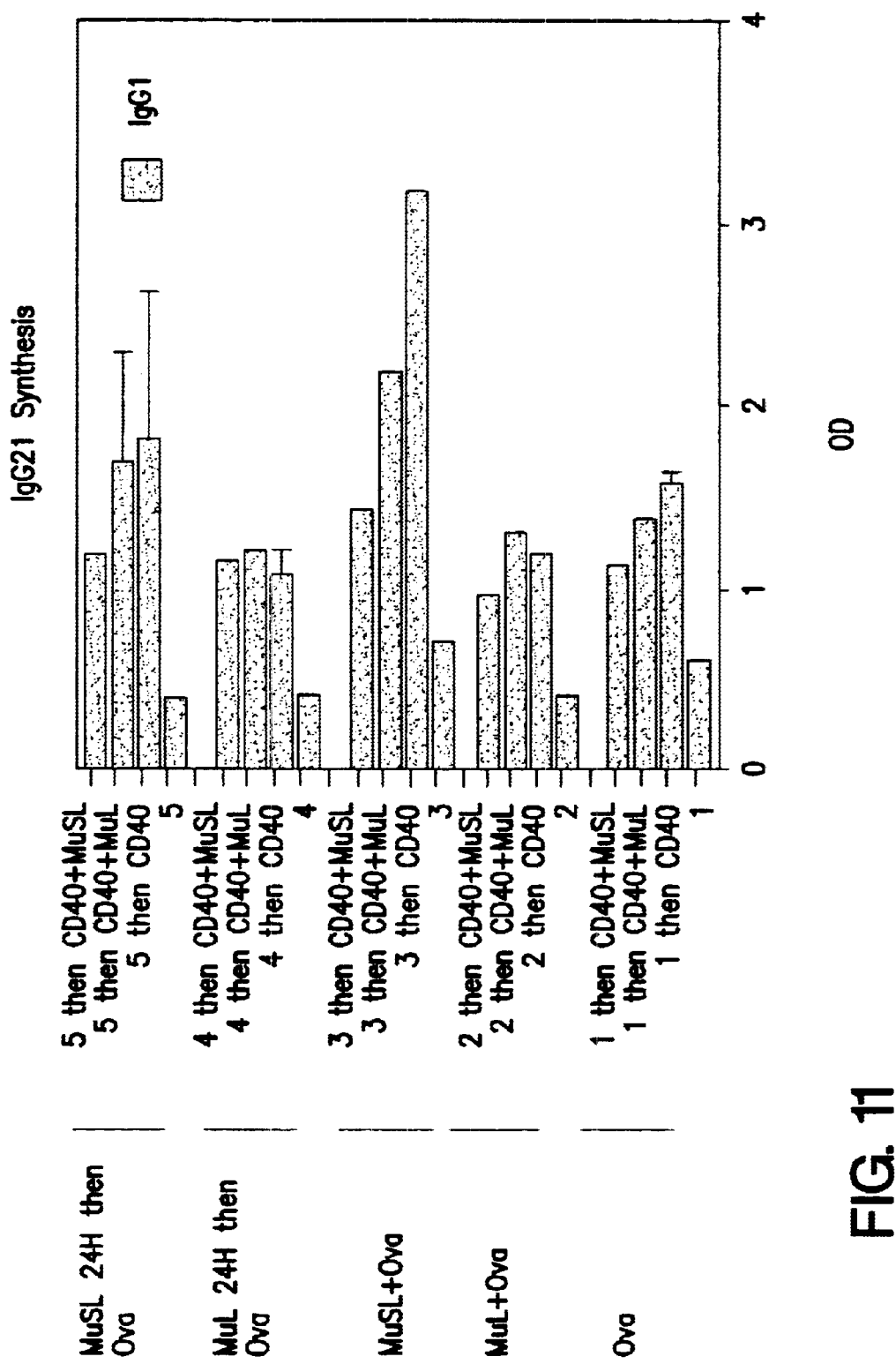

The results shown in FIGS. 10 and 11 thus confirm a polarization of the immune response towards a Th1 profile. This polarizing effect on the immune response may be observed with other antigens associated with adjuvants or otherwise.

C) Study of Lipopeptides Consisting of Fragments of the Mu Peptide i.e. of the Lipopeptides L-mIFNγ 113–132 and L-mIFNγ 122–132

Since the relatively large size of the MuL compound described above (5000 Da) is liable to limit the efficacy of its passage across the membrane, the reduction in the length of the lipopeptides sequence while at the same time preserving its activity to induce the expression of class II CMH molecules was studied on human and murine cells. Novel lipopeptides derived from IFN-γ, as well as the study of the role of the lipid chain and the determination of the minimum active compound are described below, in comparison with the results obtained with the above-mentioned MuL and MuSL peptides.

1) Experimental Section a) Peptide Synthesis and Characterization

The lipopeptide L-mIFNγ 113–132 corresponds to the peptide SEQ ID NO 1, i.e. to the fragment delimited by the amino acids located in positions 113 and 132 of murine IFNγ, the C-terminal portion of which has been modified at the carboxamide end, the said peptide being linked via its N-terminal end to an $N^\alpha$-acetyl-lysine $N^\epsilon$(palmitoyl) group (also referred to as Ac-K(Pam) or L).

The lipopeptide L-mIFNγ 122–132 corresponds to the peptide SEQ ID NO 4, i.e. to the fragment delimited by the amino acids located in positions 122 and 132 of murine IFNγ, the C-terminal portion of which has been modified at the carboxamide end, the said peptide being linked via its N-terminal activity to an Ac-K(Pam) group.

The peptides and lipopeptides were synthesized on a Rink amide resin (Senn Chemicals A. G., Dielsdorf, CH) using the Fmoc-tBu strategy (Fields, G. B. and Noble, R. L., 1990; Merrifield, R. B., 1986), and by activation with 2-(1H-benzothiazol-1-yl)-1,1,3,3-tetramethyluronium hexafluorophosphate (HBTU)-hydroxybenzotriazole (HOBt) 0.45 M in N-methylpyrrolidinone (NMP). A systematic double coupling was carried out using 4 equivalents of protected amino acids, followed by a step of systematic acetylation using acetic anhydride/DIPEA in NMP in the presence of 0.5 M HOBt in an Applied Biosystem 430 A peptide synthesizer (Foster City, USA). An Fmoc Lys(Pam)-OH group (BACHEM, Bubendorf, CH) was incorporated into the N-terminal end in order to obtain the lipopeptides.

The peptides and lipopeptides were deprotected and removed from the resin by a treatment with trifluoroacetic acid (TFA) in the presence of phenol/ethanedithiol/thioanisole/$H_2O$ (0.75 g:250 μl:250 μl:500 μl). The peptides were isolated from the TFA solution by precipitation with diethyl ether and lyophilized. Purifications were carried out by several parallel passages on RP-HPLC in a 12.5 mm×250 mm column filled with Nucleosil C18 (0.03, 5 μm) as stationary phase, using an acetonitrile/$H_2O$/0.05% TFA solvent system. The homogeneity was confirmed in two different RP-HPLC systems : all the peptides and lipopeptides are more than 90% pure. Their identity was confirmed by determining the amino acid composition after total acid hydrolysis and by determining the molecular mass by TOF-PDMS (Bio-Ion 20 Plasma Desorption Mass Spectrometer, Uppsala, Sweden). All the compounds are soluble in water.

The antepenultimate lysine 94 was introduced with a 4-methyltrityl (Mtt) protecting group for the synthesis of the fluorescent analogue of L-mIFNγ 95–132 (MuL). After selective deprotection of the Mtt group with 1% TFA in dichloromethane, the introduction onto the resin of 5(6)-carboxytetramethylrhodamine was carried out by HBTU/HUBt activation. After final deprotection with TFA and cleavage from the resin as described above, the fluorescent analogue was purified by precipitation with diethyl ether.

b) Circular Dichroism Studies

The circular dichroism measurements on the peptides were carried out at 25° C. using a Jobin-Yvon CD-6 machine at controlled temperature. The scans were carried out with a cell 0.1 cm in length in an average time of 5 sec. The wavelength interval measured ranges from 185 to 260 nm at a scanning step speed of 0.5 nm/step. The scans were carried out on the peptides at neutral pH in a 2 mM phosphate buffer with or without the helix-stabilizing reagent trifluoroethanol (TFE). The peptide concentration was adjusted to a concentration of 20 μM, after determination of the exact amount of a 100 μM solution by quantitative amino acid analysis. The average values of 4 repeat scans were expressed as average molar ellipticity per residue (deg. $cm^2$ dmol.).

c) Cell Culturing and Stimulation

Fresh splenocytes are obtained from 7-week-old female 129 Sv mice. The COLO 205 human colon carcinoma lines are obtained from the ATCC (American Type Culture Collection). The splenocytes and COLO 205 cells are maintained in RPMI 1640 (Gibco BRL, Courbevoie, France), supplemented with 10% FCS (Gibco BRL), sodium pyruvate (Sigma, St. Louis, USA) and incubated at 37° C. in 5% $CO_2$.

The cells were stimulated for 24 hours with different concentrations of MuL, L-mIFNγ 113–132, L-mIFNγ 122–132 or MuSL. The murine splenocytes and COLO 205 cells were labelled for the expression of II MHC with 1 μg of anti-mouse $IA^b$ FITC monoclonal antibody (mAb) (Pharmingen, San Diego, USA) and 10 μl of anti-HLA-DR clone TAL.1B5 mouse FITC mAb (Cymbus Biotechnology Ltd, Hants, UK), respectively. A negative control mouse FITC IgG1 (DAKO S. A., Trappes, France) was used as control isotype. The cells were incubated for 1 hour at 4° C. in PBS, 10% FCS and then washed, and the expression of II MHC was analysed by flow cytometry using a Coulter EPILS II cytometer (Coulter, Hialeah, Fla., USA) at a rate of 10,000 events per sample.

d) Immunolabelling and Fluorescence Microscopy

The intracellular passage of the lipopeptides was demonstrated in 1–$10^6$ splenocytes freshly obtained from mice, incubated for 10 minutes at 37° C. or 4° C. with 1 μM of rhodamine-labelled MuL lipopeptide. The cells were washed twice with cold PBS and fixed with 4% paraformaldehyde in PBS for 15 minutes at 4° C. The fixed cells were permeabilized with 0.05% NP-40, 1% BSA in PBS for 10 minutes at 4° C. and the non-specific sites were blocked with 2% BSA in PBS. Next, the cells were incubated with rabbit IgGs directed against the cytoplasmic domain of the α chain of IFNγ R (Santa Cruz Biotechnology, Inc., Santa Cruz, Calif., USA). This antibody was used at a dilution of 1: 100. Fluorescein-coupled sheep anti-rabbit IgGs (Santa Cruz Biotechnology, Inc.) were used as secondary antibodies at a dilution of 1: 200. The cells were then washed 4 times with PBS, mounted on slides and photographed in a Leica confocal microscope.

2) Results

All the peptides (indicated in Table 13 below) were obtained by automated solid-phase synthesis and readily purified by RP-HPLC, except for the rhodamine-labelled MuL analogue. The intercellular distribution of this fluorescent analogue was observed in the murine splenocytes after incubation for 10 min. The 38-amino-acid lipopeptide was observed in the form of aggregates in close proximity to the plasma membrane, in a distribution compatible with the localization observed by its target receptor.

TABLE 13

Physiochemical characterizations of the lipopeptides studied

| Peptide | | M.W. calculated | M.W. found | k' C3 | k' C18 |
|---|---|---|---|---|---|
| SEQ ID NO 22 | Mu | 4614 | 4613 | 20.81 | 9.46 |
| SEQ ID NO 20 | MuL | 4981 | 4983 | 26.17 | 12.68 |
| SEQ ID NO 21 | L-mIFN-γ 113–132 | 2824 | 2825 | 21.57 | 910.88 |
| SEQ ID NO 25 | L-mIFN-γ 122–132 | 1768 | 1769 | 19.85 | 10.53 |
| SEQ ID NO 24 | MuSL | 4981 | 4979 | 22.59 | 11.24 |

The molecular weights (M. W.) of the peptides were determined by mass spectrometry. The peptides were analysed by RP-HPLC in two different systems using either a Vydac C18 column (0.01–5 μm) (250×4.6 mm) or a Zorbax C3 column (0.03–5 μm) (150×4.6 mm), eluted at 50° C. with an elution rate of 1 ml/min. Composition of the solvent: A=0.05% TFA in $H_2O$, B=0.05% TFA in $H_2O$/acetonitrile (20:80), at 215 nm, using a 0–100% B linear gradient over more than 60 min. The capacity factors k'C3 and k'C. 18 were measured in the two systems.

The mechanism involved in the transmembrane transfer is passive, as could be observed after incubating the cells at 4° C., and is fast enough to avoid the complete degradation of the peptide by the exopeptidases in the culture medium.

The helical organization and the polycationic tail have been described as being essential elements for the binding of an IFN-γ agonist peptide to its receptor (Szente et al., 1996). The peptide 108–132 has been described as being the smallest peptide capable of binding to the cytoplasmic domain of IFN-γ R (Szente et al., 1996). Its capacity to induce the expression of class II CMH molecules on murine cells was reduced by a factor of 2 relative to the peptide 95–133 (Szente et al., 1996).

The crystalline structure of the homologous human cytokine (Ealick et al., 1991) shows the presence of 5 F helix turns in this portion of the molecule, corresponding to 18 of the 38 residues (47%) of biologically active C-terminal peptide. Large portions of the MuL compound have been amputated: the first 19 residues, including 3 of the 5 F helix turns, have been suppressed in the L-mIFN-γ 113–132 construct, and only 11 residues of the C-terminal portion are present in L-mIFN-γ 122–132. The cysteine found in position 133 (C-terminal end) of the cytokine has been omitted in all the lipopeptides in order to avoid their dimerization by formation of disulphide, and replaced with a simple carboxamide end in order to reinforce their stability with respect to carboxypeptidases.

Figure 12B:
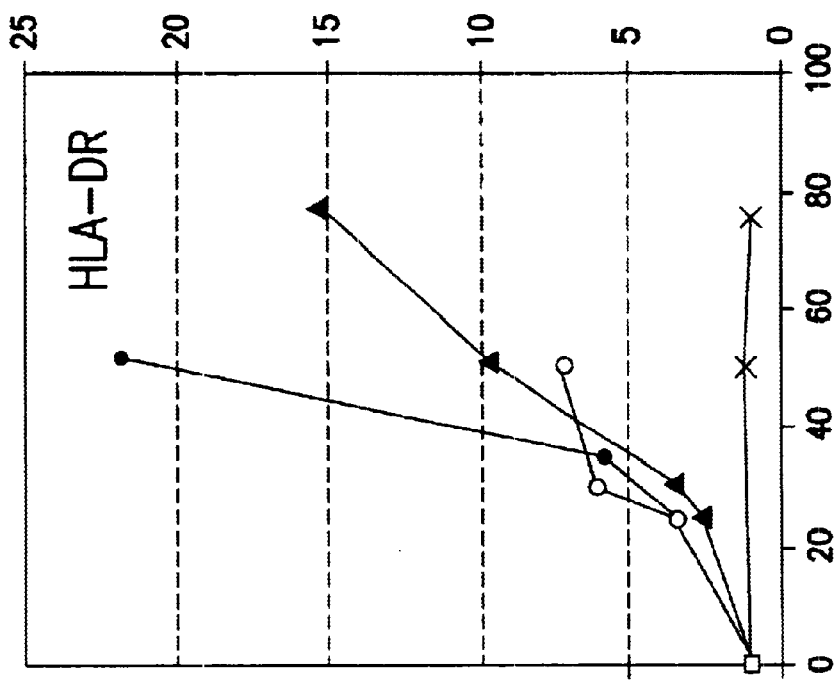
Figure 12A:
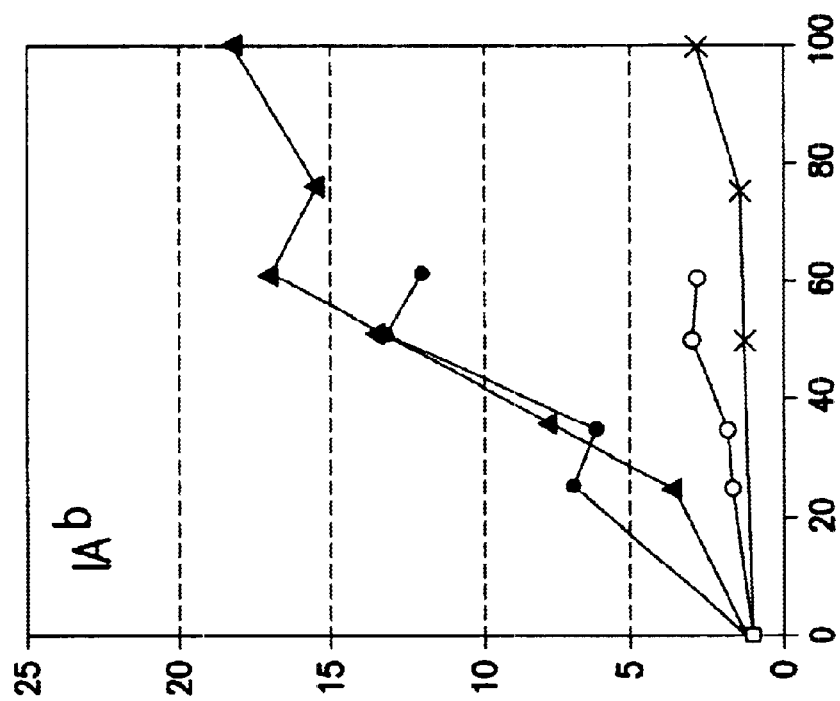

The various lipopeptides were compared on the basis of their ability to induce the expression of class II CMH molecules by murine splenocytes or human COLO 205 cell lines, incubated for 24 hours with different concentrations of lipopeptides (the non-lipid Mu peptide is inactive under these experimental conditions) (FIG. 12). A marked dose-dependent increase in the class II CMH molecules was observed on the two cell types by stimulation with MuL, or L-mIFN-γ 113–132, whereas neither L-mIFN-γ 122–132 nor MuSL are active. This result rules out the possibility of a non-specific induction of the expression of the class II CMH molecules by palmitic acid. The results indicated in FIG. 12 show that the biological activity of the truncated lipopeptide L-mIFN-γ 113–132 is equivalent to that of MuL on the splenocytes freshly obtained from mice, with a 13-fold increase in the expression of class II CMH molecules by cells stimulated with each of the lipopeptides at a concentration of 50 μM (140 or 230 μg/ml, respectively). L-mIFN-γ 113–132 is less active than MuL on the human cells, with a 10-fold increase in the expression of HLA-DR as opposed to 22-fold at a concentration of 50 μM. However, in contrast with MuL, high concentrations of truncated lipopeptide are not cytotoxic: a concentration of 75 μM (210 μg/ml) of this peptide induces a 15-fold greater expression of HLA-DR for the human cell lines, and increases by a factor of 18 the expression of $IA^b$ for the murine cells when used at a concentration of 100 μM (280 μg/ml).

Figure 13:
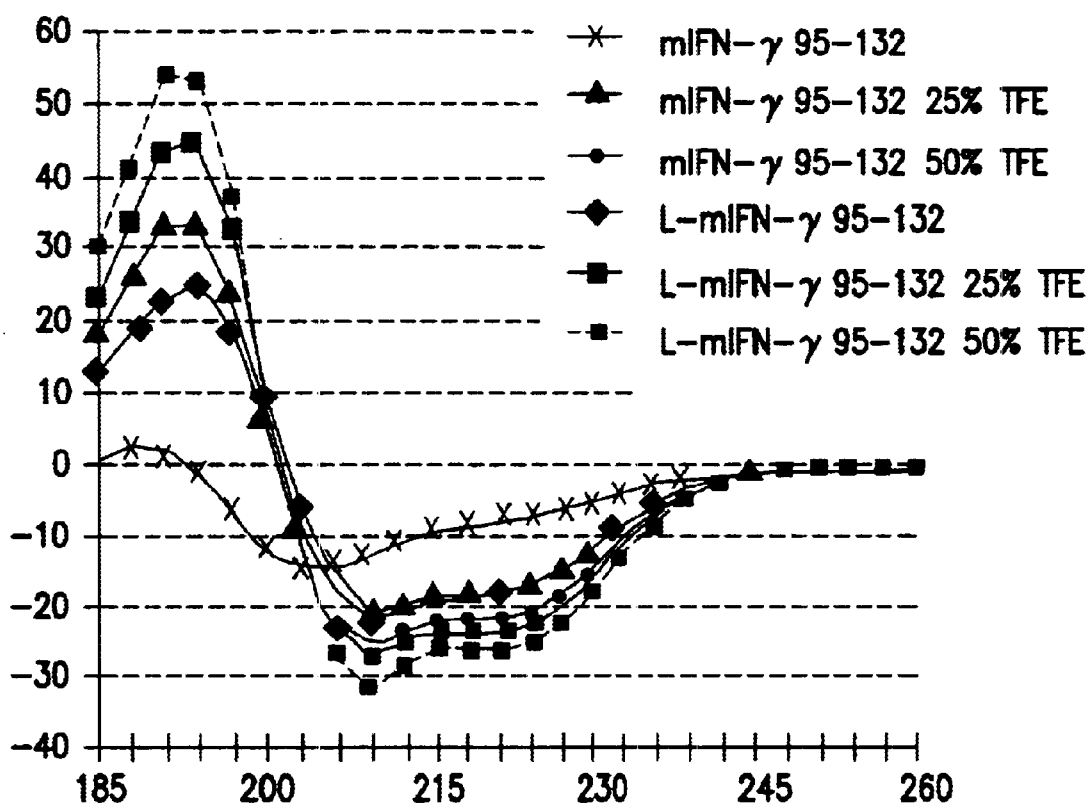

In order to further characterize the influence of the lipid modification, circular dichroism studies on the peptides and lipopeptides were carried out in order to probe the conformational changes induced in the peptide by the lipid tail. FIG. 13 shows the CD spectra for Mu and MuL, obtained in a 2 mM pH 7 phosphate buffer at ambient temperature with or without the helix-stabilizing reagent trifluoroethanol. In the aqueous buffer, a small positive ellipticity at 190 nm, and two minima at 203 and 218, suggest that the peptide is in rapid equilibrium between a poorly populated helical stage and a dominant conformation which is extended or in the form of a random coil. In the presence of trifluoroethanol, the spectrum changes to a characteristic organization with a high population of α helix with a maximum at 190 nm, and two minima at 209 and 221 nm. At 25% or 50% (by vol.) of trifluoroethanol, the ordered conformation reaches 53% or 65% respectively (considering that the value $[\theta]_{222}$ for 100% helix=33,000). It is interesting to note that the spectrum of MuL in the buffer can be superimposed on the spectrum of Mu in 25% of trifluoroethanol. The addition of 25% or 50% of trifluoroethanol to the lipopeptide solution increases the helical organization from 65% to 72% respectively, i.e. in relative proportions that are greater than the theoretical helical content of the corresponding segment in the natural cytokine.

Figures 14A, 14B:
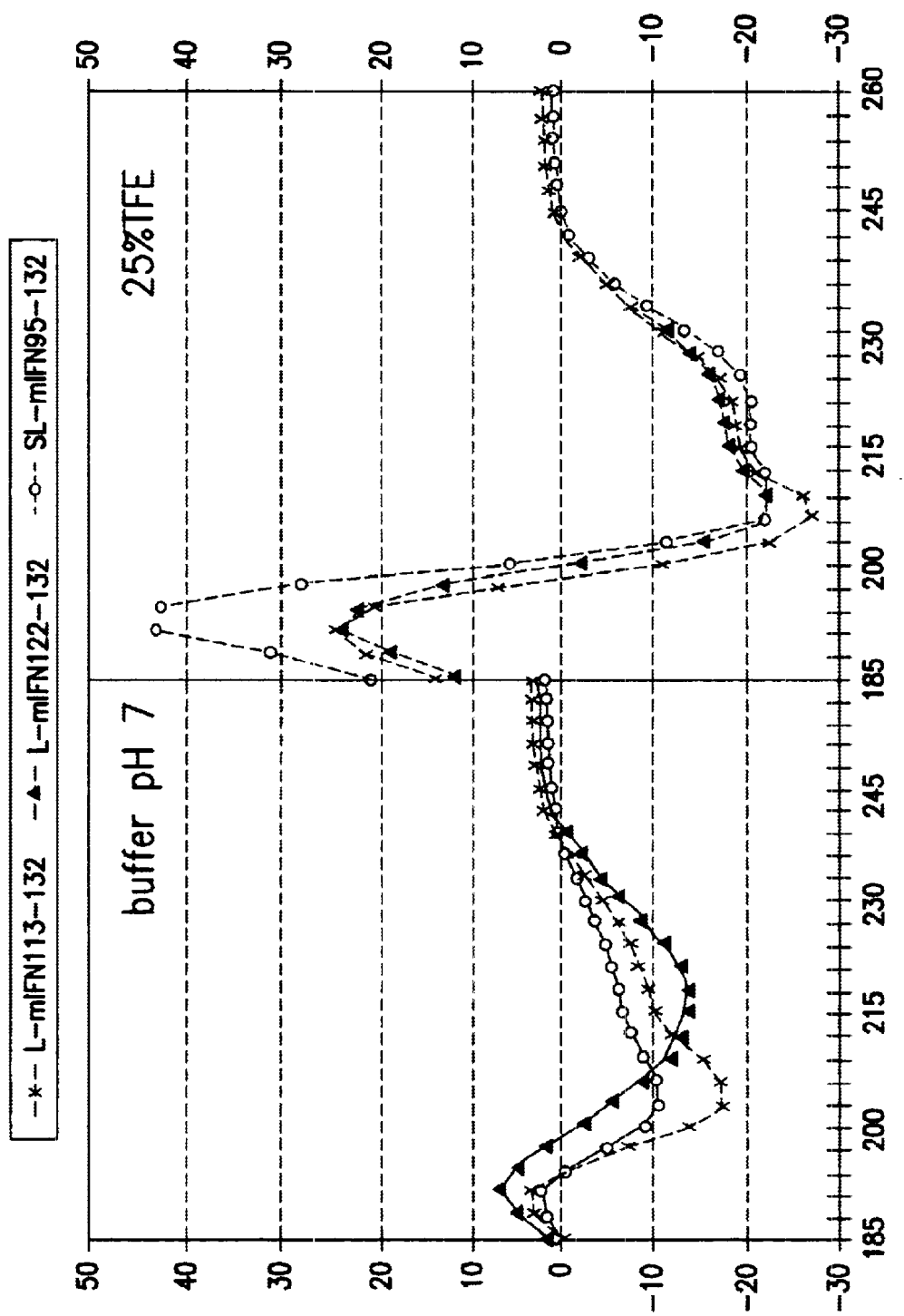

The CD spectra of the truncated and scrambled lipopeptides are indicated in FIGS. 14A (solutions in a buffer) and 14B (with 25% of trifluoroethanol): the populations with a low content of helix or of β sheet which are observed in the buffer change to approximately 50–60% helical conformation by addition of 25% of trifluoroethanol. Surprisingly, this was even observed with the 12-amino-acid lipopeptide L-mIFN-γ 122–132, despite the absence of helical organization of the end of the cytokine in its natural context.

The surprising ability of these relatively large, water-soluble compounds to cross the cell membrane passively may be linked to their tendency to spontaneously adopt an α-helical organization in water. If the liposome-lipopeptide interaction can be considered as a model for the cell-lipopeptide interaction, it may then be assumed that there is an insertion of the lipopeptides at the surface of the cells and then, in the particular case of the lipopeptides of the invention, a rapid translocation of the functional cargo sequence inside the cells, and their subsequent recognition of their target receptors.

3) Conclusion

The results given above show that the lipid modification has at least a twofold role, which contributes towards the stabilization of the helical organization of the associated peptide (even in the case of a short peptide lacking a helix) and towards its distribution in the cytoplasm. Since the shortest peptide described as being capable of binding IFN-γ R and having a weak biological activity was the peptide 108–132 (Szente et al., 1996), the maintenance of the biological activity of a peptide 5 residues shorter suggests that the lipid tail has another role which may contribute towards stabilizing the peptide-receptor binding by means of additional hydrophobic interactions.

This study illustrates the apparent capacity of functional peptides to selectively recognize the biologically significant sites of vital proteins, this being a property which is the basis of the development of large libraries of peptides as sources for the identification of ligands for various targets.

In this study, the introduction of a lipid tail improved the biological activity of the basic peptide sequence, and its ability to reach its intracellular receptor. The biological activity presented by these lipopeptide constructs derived from INF-γ confirms their use as immunomodulators. Their biologically active concentration (about a few hundred μg per ml) and their solubility in water (greater than 5 mg/ml) are compatible with volumes that are acceptable for injecting them.

Another advantage of the lipopeptides of the invention over recombinant cytokine is their good storage qualities, even in the event of an interruption of the refrigeration conditions.

BIBLIOGRAPHIC REFERENCES

Alexander, J. et al., Immunity, 1:9, 751–761 (1994)

Ben Mohamed L., et al., Eur J Immunol, 27:5, 1242–1253 (1997)

Ealick S. E., Cook W. J., Vijay-Kumar S., Carson M., Nagabhusan T. L., Trocta P. P., Bugg C. E (1991). Three-dimensional structure of the human recombinant interferon-γ. *Science*, 252:698–702

Estaquier J., et al., Molecular Immunology, 29:4, 489–499 (1992)

Fidler, I. J., Fogler, W. E., Kleinerman, E. S., Saiki, I. (1985). Abrogation of species specificity for activation of tumorocidal properties in macrophages by recombinant mouse or human interferon-γ encapsulated in liposomes. *Journal of Immunology*: 135:1289–1296.

Fields G. B., Noble R. L. (1990) Solid phase peptide synthesis utilizing 9-fluorenylmethoxy carbonyl amino acids. *Int. J Pept. Prot. Res.* 35, 161–214

Hasbold J, Johnson-Leger C, Atkins C J, Clark E A, Klaus GGB. 1994. Properties of mouse CD40: cellular distribution of CD40 and B cell activation by monoclonal anti-mouse CD40 antibodies. Eur. J. Immunol. 24;1835–1842.

Krieger J. I., et al., J Immunol, 146:7, 2331–40 (1991)

Lack G, Bradley K L, Hamelmann E, Renz H, Loader J, Leung D Y M, Larsen G, Gelfand E W. 1996. Nebulized IFN-≠5 inhibits the development of secondary allergic response in mice. *J. Immunol.* 157:1432–1439.

E. Loing, A. Delanoye, C. Sergheraert, A. Tartar, H. Gras-Masse. Assessing delivery of lipopeptides into the cytoplasm of intact cells by a functional assay based on PKC inhibition. I. The Jurkat model. *Peptide Research.*, 9, 5, 229–232 (1996)

Merrifield, R. B; J Am Soc, 85, 2149–2154 (1963)

Merrifield, R. B; Science, 232, 341–347 (1986)

Murphy K M, Heimberger A B, Loh D Y. 1990. Induction by antigen of intrathymic apoptosis of CD4$^+$ CD8$^+$ TCR$^{10}$ thymocytes in vivo. Science 250;1720–1723.

Panina-Bordignon P., et al., Eur J Immunol, 19:12, 2237–2242 (1989)

Sanceau, J., Sondermeyer, P., Beranger, F., Falcoff, R., Vaquero, C. (1I987). Intracellular human g—interferon triggers an antiviral state in transformed murine L cells. *Proceedings of the National Academy of sciences of USA*. 84:2906–2910.

Sareneva T; Pirhonen J; Cantell K; Julkunen I N-glycosylation of human interferon-gamma:glycans at Asn-25 are critical for protease resistance. Biochem J 308 (Pt 1): 9–14 (1995)

Smith M R; Muegge K; Keller J R; Kung H F; Young H A; Durum S K Direct evidence for an intracellular role for IFN-gamma. Microinjection of human IFN-gamma induces Ia expression on murine macrophages. J Immunol 144 :1777–82 (1990)

Szente B E; Johnson H M ; Binding of IFN gamma and its C-terminal peptide to a cytoplasmic domain of its receptor that is essential for function. Biochem Biophys Res Commun 201:215–21 (1994)

Szente B E; Soos J M; Johnson H M; The C-terminus of IFN-gamma is sufficient for intracellular function. Biochem Biophys Res Commun 203:1645–54 (1994)

Szente B E; Subramaniam P S; Johnson H M; Identification of IFN-gamma receptor binding sites for JAK2 and enhancement of binding by IFN-gamma and its C-terminal peptide IFN-gamma (95–133). J Immunol 155:5617–22 (1995)

Szente B E; Weiner I J; Jablonsky M J; Krishna N R; Torres B A; Johnson H M (Department of Microbiology and Cell Science, University of Florida, Gainesville 32611, USA.) Structural requirements for agonist activity of a murine interferon-gamma peptide. J Interferon Cytokine Res 16 :813–7 (1996)

Tam P. and Spetzler J. C., Biomedical Peptides, Proteins & Nucleic Acids, 1, 123–132 (1995)

Thiam, K., Loing, E., Gilles, F., Verwaerde, C., Quatannens, B., Sergheraert, C., Auriault, C., Gras-Masse, H. Induction of apoptosis by PKC-pseudosubstrate lipopeptides in several human cells. *Letters In Peptide Sciences*, 4, 1–6, 1997.

KEY TO THE FIGURES

FIG. 1: Histogram representing the induction of VCAM-1 on human dermal cells (HMVECd). The results are expressed as an expression index, giving the activity of human IFN-γ (500 U/ml; 75 ng/ml) a value of 1. The columns from left to right correspond respectively to the results obtained:

without treating the said cells, by treating the cells with human IFN-γ at 500 U/ml, by treating the cells with TNF at 10 ng/ml, by treating the cells with a mixture of human IFN-γ at 500 U/ml and TNF at 10ng/ml, by treating the cells with the MuSL peptide at 25 µM, by treating the cells with the MuSL peptide at 50 µM, by treating the cells with the MuL peptide at 25 µM, by treating the cells with the MuL peptide at 50 µM.

FIG. 2: Histogram representing the results of the antiviral test carried out on L929 fibroblasts treated with the MuSL or MuL peptides. The results are expressed as optical density (OD). The columns from left to right correspond respectively to the measurements carried out:

on cells not infected with VSV, on cells infected with VSV and not treated with MuSL or MuL, on cells infected with VSV and treated with MuSL (white columns) or MuL (black columns) at 1 µM, 2 µM, 3 µM, 4 µM, 5 µM, 6 µM, 7 µM, 8 µM, 9 µM, 10 µM FIG. 3: Histogram representing the results of the antiviral test carried out on L929 fibroblasts treated with recombinant IFN-γ. The results are expressed as optical density (OD). The columns from left to right correspond respectively to the measurements carried out:

on cells not infected with VSV, on cells infected with VSV and not treated with recombinant IFN-γ, on cells infected with VSV and treated with recombinant IFN-γ at 0.18 IU, 0.38 IU, 0.75 IU, 1.5 IU, 3.12 IU, 6.25 IU, 12.5 IU, 25 IU, 50 IU, 100 IU, 200 IU.

FIG. 4: Proliferative effect of the anti-CD40+IL-4 stimulation on murine splenocytes. Inhibition by MuL of the biological activity of murine IL-4.

FIG. 5: Proliferative effect of the anti-CD40+IL-4 stimulation on murine splenocytes taken from IFN-γR KO animals. In the absence of a functional IFN-γ receptor, no inhibitory activity of MuL is observed.

FIG. 6: Proliferative effect of the anti-CD40+IL-4 stimulation on murine splenocytes taken from WT animals. The presence of a functional IFN-γ receptor is necessary for MuL to be able to inhibit the biological activity of IL-4.

FIG. 7: Synthesis of IgG2a by murine splenocytes stimulated in vitro by anti-CD40, in the presence or absence of MuL.

FIG. 8: Synthesis of IgG1 by murine splenocytes stimulated in vitro by anti-CD40, in the presence or absence of MuL.

FIG. 9: Synthesis of total IgGs by murine splenocytes stimulated in vitro by anti-CD40, in the presence or absence of MuL.

FIG. 10: Production of IgG2a by the splenocytes of animals immunized according to the various conditions described in the procedure and re-stimulated in vitro under the conditions noted on the y-axis. The quantification of the synthesis of IgG2a is carried out by ELISA.

FIG. 11: Production of IgG1 by the splenocytes of animals immunized according to the various conditions described in the procedure and re-stimulated in vitro under the conditions noted on the y-axis. The quantification of the synthesis of IgG1 is carried out by ELISA.

FIG. 12: Induction of class II CMH molecules by human or murine cells stimulated with lipopeptides derived from IFN-γ. The murine splenocytes (A) and the COLO 205 human cell line (B) were incubated for 24 hours with different concentrations of lipopeptides derived from IFN-γ. The cells were labelled with a monoclonal antibody directed against the class II CMH molecules, and analysed by flow cytometry. The ratio between the average fluorescence intensity of the cells treated with the lipopeptides and between the average fluorescence intensity of the untreated cells is indicated on the y-axis. The lipopeptide concentration is indicated in μM on the x-axis; MuL: solid circles; MuSL : hollow circles ; L-mIFN 113–132: triangles; L-mIFN 122–132: X.

FIG. 13: CD (circular dichroism) spectra of Mu and MuL at a concentration of 20 μM in a 2 mM pH 7 phosphate buffer without PFE (mIFN 95–132: X; L-IFN 95–132: diamonds), with 25% of TFE (mIFN 95–132: triangles); L-mIFN 95–132: large squares), or with 50% of TFE (mIFN 95–132: circles; L-mIFN 95–132: small squares). Temperature: 298 K. The values indicated on the y-axis correspond to Theta×$10^{-3}$ (deg.cm$^2$.dmo$^{-1}$), and those indicated on the x-axis correspond to wavelengths (nm).

FIG. 14: CD spectra of L-mIFN 113–132, L-mIFN 122–132 and MuSL, at a concentration of 20 μM in a 2 mM pH 7 phosphate buffer (FIG. 14A), or in the presence of 25% of TFE (FIG. 14B); (L-mIFN 113–132: triangles; L-mIFN 122–132: X; MuSL: hollow circles). The values indicated on the y-axis correspond to Theta×$10^{-3}$ (deg.cm$^2$.dmo$^{-1}$), and those indicated on the x-axis correspond to wavelengths (nm).

TABLE 1 epitopes of chronic myeloid leukaemia

| Peptide | Sequence | Binding to HLA |
|---|---|---|
| 247–255 | (SEQ ID NO 26) | B44 |
| 488–496 | (SEQ ID NO 27) | B44 |
| 768–776 | (SEQ ID NO 28) | B44 |
| 901–934 b2a2 | (SEQ ID NO 29) | B44 |
| 902–935 b2a2 | (SEQ ID NO 30) | B44 |
| 986–994 | (SEQ ID NO 31) | B44 |
| 1176–1184 | (SEQ ID NO 32) | B44 |
| 1252–1260 | (SEQ ID NO 33) | B44 |
| 1691–1699 | (SEQ ID NO 34) | B44 |
| 49–57 | (SEQ ID NO 35) | B8 |
| 580–588 | (SEQ ID NO 36) | B8 |
| 722–730 | (SEQ ID NO 37) | B8 |
| 786–794 | (SEQ ID NO 38) | B8 |
| 886–893 | (SEQ ID NO 39) | 88 |
| 928–936 b3a2 | (SEQ ID NO 40) | B8 |
| 1830–1838 | (SEQ ID NO 41) | B8 |

TABLE 1-continued epitopes of chronic myeloid leukaemia

| Peptide | Sequence | Binding to HLA |
|---|---|---|
| 1975–1983 | (SEQ ID NO 42) | B8 |
| 1977–1984 | (SEQ ID NO 43) | B8 |
| 252–260 | (SEQ ID NO 44) | B7 |
| 329–338 | (SEQ ID NO 45) | B7 |
| 693–701 | (SEQ ID NO 46) | B7 |
| 1058–1066 | (SEQ ID NO 47) | B7 |
| 1196–1205 | (SEQ ID NO 48) | B7 |
| 1560–1569 | (SEQ ID NO 49) | B7 |
| 1717–1725 | (SEQ ID NO 50) | B7 |
| 1878–1884 | (SEQ ID NO 51) | B7 |
| 36–44 | (SEQ ID NO 52) | B27 |
| 71–79 | (SEQ ID NO 53) | B27 |
| 575–583 | (SEQ ID NO 54) | B27 |
| 834–842 | (SEQ ID NO 55) | B27 |
| 642–650 | (SEQ ID NO 56) | A2 |
| 684–692 | (SEQ ID NO 57) | A2 |
| 708–716 | (SEQ ID NO 58) | A2 |
| 714–722 | (SEQ ID NO 59) | A2 |
| 817–825 | (SEQ ID NO 60) | A2 |
| 881–889 | (SEQ ID NO 61) | A2 |
| 908–917 | (SEQ ID NO 62) | A2 |
| 912–920 | (SEQ ID NO 63) | A2 |
| 1240–1248 | (SEQ ID NO 64) | A2 |
| 1903–1911 | (SEQ ID NO 65) | A2 |
| 1932–1940 | (SEQ ID NO 66) | A2 |
| 50–58 | (SEQ ID NO 67) | A1 |
| 223–231 | (SEQ ID NO 68) | A1 |
| 549–558 | (SEQ ID NO 69) | A3/A11 |
| 583–591 | (SEQ ID NO 70) | A3/A11 |
| 715–724 | (SEQ ID NO 71) | A3/A11 |
| 916–923 | (SEQ ID NO 72) | A3/A11 |
| 920–928 b3a2 | (SEQ ID NO 73) | A3/A11 |
| 924–932 b3a2 | (SEQ ID NO 74) | A3/A11 |
| 1156–1165 | (SEQ ID NO 75) | A3/A11 |
| 1311–1320 | (SEQ ID NO 76) | A3/A11 |
| 1499–1509 | (SEQ ID NO 77) | A3/A11 |
| 1724–1734 | (SEQ ID NO 78) | A3/A11 |
| 1905–1914 | (SEQ ID NO 79) | A3/A11 |
| 1922–1930 | (SEQ ID NO 80) | A3/A11 |
| 924–936 b3a2 | (SEQ ID NO 81) | DR4 |

TABLE 2 epitopes of p53

| | |
|---|---|
| epitopes of p53 binding to HLA-A1 | |
| (SEQ ID NO 82) | (196–205) |
| (SEQ ID NO 83) | (226–234) |
| epitopes of p53 binding to HLA-A2 | |
| (SEQ ID NO 84) | (25–35) |
| (SEQ ID NO 85) | (65–73) |
| (SEQ ID NO 86) | |
| (SEQ ID NO 87) | (129–137) |
| (SEQ ID NO 88) | (149–157) |
| (SEQ ID NO 89) | (187–197) |
| (SEQ ID NO 90) | (264–272) |
| (SEQ ID NO 91) | (322–330) |
| epitopes of p53 binding to HLA-A3 | |
| (SEQ ID NO 92) | (156–164) |
| (SEQ ID NO 93) | (282–290) |
| (SEQ ID NO 94) | (298–306) |
| epitopes of p53 binding to HLA-B7 | |
| (SEQ ID NO 95) | (26–35) |
| (SEQ ID NO 96) | (63–73) |
| (SEQ ID NO 97) | |
| (SEQ ID NO 98) | (189–197) |
| (SEQ ID NO 99) | (249–257) |
| (SEQ ID NO 100) | (321–330) |

TABLE 2-continued epitopes of p53 epitopes of p53 binding to HLA-B8

| | |
|---|---|
| (SEQ ID NO 101) | (135–143) |
| (SEQ ID NO 102) | (187–195) |
| (SEQ ID NO 103) | (210–218) | epitopes of p53 binding to HLA-B51

| | |
|---|---|
| (SEQ ID NO 104) | (25–35) |
| (SEQ ID NO 105) | (65–73) |
| (SEQ ID NO 106) | (194–203) |

TABLE 3 epitopes of human melanoma

| Gene/protein | MHC restriction | Peptide | Position of the amino acids |
|---|---|---|---|
| Tyrosinase | HLA-A2 | (SEQ ID NO 107) | 1–9 |
| | HLA-A2 | (SEQ ID NO 108) | 369–377 |
| | | (SEQ ID NO 109) | |
| | HLA-A24 | (SFQ ID NO 110) | 206–214 |
| | HLA-B44 | (SEQ ID NO 111) | 192–200 |
| | HLA-DR4 | (SEQ ID NO 112) | 56–70 |
| | | (SEQ ID NO 113) | 450–462 |
| Pmel17$^{gp100}$ | HLA-A2 | (SEQ ID NO 114) | 154–162 |
| | HLA-A2 | (SEQ ID NO 115) | 177–186 |
| | HLA-A2 | (SEQ ID NO 116) | 178–186 |
| | HLA-A2 | (SEQ ID NO 117) | 209–217 |
| | HLA-2 | (SEQ ID NO 118) | 280–288 |
| | HLA-A2 | (SEQ ID NO 119) | 457–466 |
| | | (SEQ ID NO 120) | |
| | HLA-A2 | (SEQ ID NO 121) | |
| | HLA-A2 | (SEQ ID NO 122) | 570–579 |
| | HLA-A3 | | 17–25 |
| Melan-A$^{MART-1}$ | HLA-A2 | (SEQ ID NO 123) | 26(7)–35 |
| | HLA-A2 | (SEQ ID NO 124) | 32–40 |
| gp$^{75TRP-1}$ | HLA-A31 | (SEQ ID NO 125) | |
| TRP-2 | HLA-A31 | (SEQ ID NO 126) | 197–205 |

TABLE 4 epitopes of tumours resulting from mutations

| Gene/protein | Tumour | MHC restriction | Peptide | Position of the amino acids |
|---|---|---|---|---|
| MUM-1 | Melanoma | HLA-B44 | (SEQ ID NO 127) | 30–38 |
| CDK4 | Melanoma | HLA-A2 | (SEQ ID NO 128) | 23–32 |
| β-catenin | Melanoma | HLA-A24 | (SEQ ID NO 129) | 29–37 |
| HLA-A2 | renal carcinoma | — | — | — |
| CASP-8 | squamous carcinoma of the head and neck | HLA-B35 | (SEQ ID NO 130) | 476–484 |

TABLE 5 antigens common to various tumours

| Gene | tissue in which normal expression takes place | MHC restriction | Antigenic peptide | Position of the amino acids |
|---|---|---|---|---|
| MAGE-1 | testicles | HLA-A1 | (SEQ ID NO 131) | 161–169 |
| | | HLA-Cw16 | (SEQ ID NO 132) | 230–238 |
| MAGE-3 | testicles | HLA-A1 | (SEQ ID NO 133) | 168–176 |
| | | HLA-A2 | (SEQ ID NO 134) | 271–279 |
| | | HLA-B44 | (SEQ ID NO 135) | 167–176 |
| BAGE | testicles | HLA-Cw16 | (SEQ ID NO 136) | 2–10 |
| GAGE-1/2 | testicles | HLA-Cw6 | (SEQ ID NO 137) | 9–16 |
| RAGE-1 | retina | HLA-B7 | (SEQ ID NO 138) | 11–20 |
| GnTV | none | HLA-A2 | (SEQ ID NO 139) | 38–64 |
| mucin | breasts during lactation | no restrictions | (SEQ ID NO 140)* | |

*aberrant N-acetyl glucosaminyl transferase V (GnTV) transcript found only in the melanomas.

TABLE 6 epitopes of the HIV-1 virus

| | |
|---|---|
| HLA-A1 | (Nef 96–106: (SEQ ID NO 141) |
| | (Nef 121–128 (SEQ ID NO 142) |
| | (Nef 137–145: (SEQ ID NO 143) |
| | (Nef 184–191: (SEQ ID NO 144) |
| | (Nef 195–202: (SEQ ID NO 145) |
| HLA-A2 | Gp120 121–129: (SEQ ID NO 146) |
| | P17 77–85: (SEQ ID NO 147) |
| | RT 200–208: (SEQ ID NO 148) |
| | RT 275–285: (SEQ ID NO 149) |
| | RT 346–354: (SEQ ID NO 150) |
| | RT 368–376: (SEQ ID NO 151) |
| | RT 376–387: (SEQ ID NO 152) |
| | RT 476–484: (SEQ ID NO 153) |
| | RT 588–596: (SEQ ID NO 154) |
| | RT 683–692: (SEQ ID NO 155) |
| | Nef 136–145: (SEQ ID NO 156) |
| | Nef 180–189: (SEQ ID NO 157) |
| | Nef 190–198: (SEQ ID NO 158) |
| | Gp41 818–826: (SEQ ID NO 159) |
| | P24 185–193: (SEQ ID NO 160) |
| | RT 346–354: (SEQ ID NO 161) |
| | RT 588–596: (SEQ ID NO 162) |
| | Pro 143–152: (SEQ ID NO 163) |
| | (Gp 120 37–44: (SEQ ID NO 164) |
| | (Gp 120 115–122: (SEQ ID NO 165) |
| | (Gp 120 313–321: (SEQ ID NO 166) |
| | (Gp 120 197–205: (SEQ ID NO 167) |
| | (Gp 120 428–435: (SEQ ID NO 168) |
| | (Gp 41 836–844: (SEQ ID NO 169) |
| | (p24 219–228: (SEQ ID NO 170) |
| | (p15 422–431: (SEQ ID NO 171) |
| | (p15 448–456: (SEQ ID NO 172) |
| | (RT 681–691: (SEQ ID NO 173) |
| HLA-A3 | P17 18–26: (SEQ ID NO 174) |
| | P17 20–28: (SEQ ID NO 175) |
| | RT 200–210: (SEQ ID NO 176) |
| | RT 325–333: (SEQ ID NO 177) |
| | RT 359–368: (SEQ ID NO 178) |
| | Nef 73–82: (SEQ ID NO 179) |
| | Gp 120 37–46: (SEQ ID NO 180) |
| | Gp41 775–785: (SEQ ID NO 181) |
| | P17 18–26: (SEQ ID NO 182) |

TABLE 6-continued epitopes of the HIV-1 virus

| | |
|---|---|
| HLA-A11 | RT 325–333: (SEQ ID NO 183) |
| | RT 507–517: (SEQ ID NO 184) |
| | Nef 73–82: (SEQ ID NO 185) |
| | Nef 84–92: (SEQ ID NO 186) |
| | p24 349–359: (SEQ ID NO 187) |
| | P17 83–91: (SEQ ID NO 188) |
| HLA-A24 (A9) | Gp120 52–61: (SEQ ID NO 189) |
| | Gp41 591–598: (SEQ ID NO 190) |
| | or 590–597: (SEQ ID NO 191) |
| | (RT 484–492: (SEQ ID NO 192) |
| | (RT 508–516: (SEQ ID NO 193) |
| | (RT 681–691: (SEQ ID NO 194) |
| HLA-A25 (A10) | P24 203–212: (SEQ ID NO 195) |
| HLA-A26 (A10) | P24 167–175: (SEQ ID NO 196) |
| HLA-A30 (A19) | (Gp41 845–852: (SEQ ID NO 197) |
| HLA-A31 (A19) | Gp41 775–785: (SEQ ID NO 198) |
| HLA-A32 (A19) | Gp120 424–432: (SEQ ID NO 199) |
| | Gp41 774–785: (SEQ ID NO 200) |
| | RT 559–568: (SEQ ID NO 201) |
| HLA-A33 (A19) | (P24 266–275: (SEQ ID NO 202) |
| HLA-B7 | RT 699–707: (SEQ ID NO 203) |
| | Nef 68–77: (SEQ ID NO 204) |
| | Nef 128–137: (SEQ ID NO 205) |
| | Gp120 303–312: (SEQ ID NO 206) |
| | Gp41 848–856: (SEQ ID NO 207) |
| | RT 699–707: (SEQ ID NO 208) |
| HLA-B8 | Gp120 2–10: (SEQ ID NO 209) |
| | P17 24–32: (SEQ ID NO 210) |
| | Nef 90–97: (SEQ ID NO 211) |
| | P24 259–267: (SEQ ID NO 212) |
| | Gp41 591–598: (SEQ ID NO 213) |
| | (Gp41 849–856: PRRIRQGL (SEQ ID NO 214) |
| | or 851–859: RIRQGLERIL (SEQ ID NO 215) |
| | (P24 329–337: (SEQ ID NO 216) |
| | (RT 185–193: (SEQ ID NO 217) |
| | (Nef 182–189: (SEQ ID NO 218) |
| HLA-B14 | Gp4l 589–597: (SEQ ID NO 219) |
| | P24 298–306: (SEQ ID NO 220) |
| | (P24 183–191 ?: (SEQ ID NO 221) |
| | (p24 304–313: (SEQ ID NO 222) |
| | (p24 305–313: (SEQ ID NO 223) |
| HLA-B18 | Nef 135–143: (SEQ ID NO 224) |
| | Nef 135–143: (SEQ ID NO 225) |
| HLA-B27 | P24 263–272: (SEQ ID NO 226) |
| | Nef 73–82: (SEQ ID NO 227) |
| | Nef 134–141: (SEQ ID NO 228) |
| | or 133–141: (SEQ ID NO 229) |
| | Gp41 589–597: (SEQ ID NO 230) |
| | (Gp41 791–800: (SEQ ID NO 231) |
| HLA-B35 | Gp120 78–86: (SEQ ID NO 232) |
| | Gp120 257–265: (SEQ ID NO 233) |
| | RT 285–294: (SEQ ID NO 234) |
| | RT 323–331: (SEQ ID NO 235) |
| | RT 342–350: (consensus clade B) (SEQ ID NO 236) |
| | RT 460–468: (SEQ ID NO 237) |
| | RT 598–608: (SEQ ID NO 238) |
| | Nef 68–76: (SEQ ID NO 239) |
| | Nef 74–81: (SEQ ID NO 240) |
| | Gp41 611–619: (SEQ ID NO 241) |
| | Gp120 42–52: (SEQ ID NO 242) |
| | P17 124–132: (consensus clade B) (SEQ ID NO 243) |
| | P24 254–262: (consensus clade B) (SEQ ID NO 244) |
| HLA-B37 | Nef 120–128: (SEQ ID NO 245) |
| HLA-B44 (B12) | P24 178–186: (SEQ ID NO 246) |
| | (p24 175–184: (SEQ ID NO 247) |
| HLA-B51 (B5) | gp41 562–570: (SEQ ID NO 248) |
| | RT 200–208: (SEQ ID NO 249) |
| | RT 209–217: (SEQ ID NO 250) |
| | RT 295–302: (SEQ ID NO 251) |
| HLA-B52 (B5) | Nef 190–198: (SEQ ID NO 252) |
| HLA-B55 (B22) | Gp120 42–51: (SEQ ID NO 253) |
| HLA-B57 and B58 (B17) | P24 240–249: (SEQ ID NO 254) |
| | Nef 116–125: (SEQ ID NO 255) |
| | or 116–124: (SEQ ID NO 256) |
| | Nef 120–128: (SEQ ID NO 257) |
| | (P24 147–155: (SEQ ID NO 258) |
| | (P24 164–172: (SEQ ID NO 259) |
| HLA-Bw62 (B15) | P17 20–29: (SEQ ID NO 260) |
| | P24 268–277: (SEQ ID NO 261) |
| | RT 427–438: (SEQ ID NO 262) |
| | Nef 84–91: (SEQ ID NO 263) |
| | Nef 117–127: (SEQ ID NO 264) |
| HLA-Cw4 | gp120 380–388: (SEQ ID NO 265) |
| HLA-Cw8 | RT 663–672: (SEQ ID NO 266) |
| | P24 305–313: (SEQ ID NO 267) |
| | Nef 82–91: (SEQ ID NO 268) |
| HLA-Cw? | P24 308–316: (SEQ ID NO 269) |

TABLE 7 epitopes of the E6 and E7 proteins (E7 11–20) (SEQ ID NO 270)
(E7 82–90) (SEQ ID NO 271)
(E7 86–93) (SEQ ID NO 272)
(E6 29–38) (SEQ ID NO 273)
(E6 18–26) (SEQ ID NO 274)
(E6 8–15) (SEQ ID NO 275)
(E6 45–67) (SEQ ID NO 276)
(E6 80–88) (SEQ ID NO 277)
(E6 121–140) (SEQ ID NO 278)
(E7 43–57) (SEQ ID NO 279)
(E7 44–52) (SEQ ID NO 280)
(E7 46–55) (SEQ ID NO 281)

What is claimed is:

1. An isolated lipopeptide, comprising:

a peptide which binds to an interferon-gamma (IFN-γ) receptor intracellularly, but which does not bind to the IFN-γ receptor extracellularly, said peptide consists of a peptide sequence delimited by amino acids located in positions 95 and 133 or 132 of murine LFN-γ, reference SEQ ID NO:17; and a lipophilic molecule selected from the group consisting of a linear or branched, saturated or unsaturated C4 to C20 hydrocarbon-based chain, and a steroid group, said steroid group optionally linked to said hydrocarbon-based chain, wherein said lipophilic molecule is covalently linked to the peptide and is optionally combined with a short vector peptide comprising a group that is ionized at physiological pH, and a group for covalently bonding to said hydrocarbon-based chain or said steroid group.

2. The lipopeptide according to claim 1, wherein said lipophilic molecule is a hydrocarbon-based chain selected from the group consisting of palmitic acid, oleic acid, linoleic acid, and linolenic acid.

3. The lipopeptide according to claim 1, wherein said lipophilic molecule is a steroid group, said steroid group is a cholesterol selected from the group consisting of cholest-5-enyl-3-oxyacetic acid and cholest-5-enyl-3-oxycarbonic acid.

4. The lipopeptide according to claim 1, wherein said lipophilic molecule is covalently bonded to one or more amino acids of the peptide.

5. The lipopeptide according to claim 1, wherein said lipophilic molecule is covalently bonded to an $\alpha NH_2$ or $\epsilon NH_2$ group of a lysine located in N-terminal or C-terminal position of the peptide, or to any amino, alcohol or thiol group optionally added to the peptide with a spacer.

6. The lipopeptide according to claim 1, wherein a COOH group of the C-terminal amino acid is substituted with a group and the substituted lipopentide is resistant to exopeptidases.

7. The lipopeptide according to claim 1, wherein the lipophilic molecule is $N^{\alpha}$-acetyl-Lysine $N^{\epsilon}$(palmitoyl) group, and wherein the lipopeptide is selected from the group consisting of a sequence delimited by the amino acids located in positions 95 and 132 of the murine IFN-γ peptide sequence (reference SEQ ID NO:17), consisting of SEQ ID NO:20, and a sequence delimited by the amino acids located in positions 113 and 132 of the murine IFN-γ peptide sequence, consisting of SEQ ID NO:21.

8. A micelle or micro-aggregate of the lipopeptide according to claim 1, wherein said micelle or micro-aggregate is less than 1 μm in size.

9. The micelle or micro-aggregate according to claim 8, obtained by dispersing the lipopeptide in about 80% concentrated acetic acid solution.

10. A pharmaceutical composition comprising a lipopeptide according to claim 1, in combination with a carrier in a physiologically acceptable pharmaceutical formulation.

11. An isolated peptide delimited on the N-terminal side by an amino acid located in position 113 to 121, and on the C-terminal side by an amino acid located in position 132 of the murine IFN-γ peptide sequence (reference SEQ ID NO:17), represented by SEQ ID NO:1.

* * * * *